(12) United States Patent
Knowland et al.

(10) Patent No.: US 9,002,438 B2
(45) Date of Patent: Apr. 7, 2015

(54) SYSTEM FOR THE DETECTION OF GAMMA RADIATION FROM A RADIOACTIVE ANALYTE

(71) Applicants: Joshua G. Knowland, Cary, NC (US); Charles W. Scarantino, Raleigh, NC (US); Ronald K. Lattanze, Morrisville, NC (US)

(72) Inventors: Joshua G. Knowland, Cary, NC (US); Charles W. Scarantino, Raleigh, NC (US); Ronald K. Lattanze, Morrisville, NC (US)

(73) Assignee: Lucerno Dynamics, Raleigh, NC (US)

( * ) Notice: Subject to any disclaimer, the term of this patent is extended or adjusted under 35 U.S.C. 154(b) by 79 days.

(21) Appl. No.: 13/840,925

(22) Filed: Mar. 15, 2013

(65) Prior Publication Data

US 2013/0324844 A1    Dec. 5, 2013

Related U.S. Application Data

(60) Provisional application No. 61/653,014, filed on May 30, 2012.

(51) Int. Cl.
*A61B 6/00*    (2006.01)
(52) U.S. Cl.
CPC .................................... *A61B 6/4258* (2013.01)
(58) Field of Classification Search
USPC .................. 600/407, 431, 436; 250/252, 363, 250/370.11, 370.08
See application file for complete search history.

(56) References Cited

U.S. PATENT DOCUMENTS

| | | | |
|---|---|---|---|
| 4,629,894 A | 12/1986 | Lelong | |
| 4,692,890 A | 9/1987 | Arseneau | |
| 4,881,171 A | 11/1989 | Jatteau et al. | |
| 5,309,357 A | 5/1994 | Stark et al. | |
| 5,821,538 A | 10/1998 | De Antoni et al. | |
| 6,448,544 B1 * | 9/2002 | Stanton et al. | 250/208.1 |
| 8,680,476 B2 * | 3/2014 | Webster et al. | 250/374 |
| 2002/0137991 A1 | 9/2002 | Scarantino et al. | |
| 2003/0012731 A1 | 1/2003 | Suddarth et al. | |

(Continued)

FOREIGN PATENT DOCUMENTS

| | | |
|---|---|---|
| WO | WO 2007140352 A2 | 12/2007 |
| WO | WO 2009158143 A1 | 12/2009 |
| WO | WO 2010-039298 | 4/2010 |

OTHER PUBLICATIONS

Son, C., An implantable Wireless Microdosimeter for Radiation Oncology, School of Electrical and Computer Engineering, Mems 2008, Jan. 13-17, 2008, pp. 256-259.

(Continued)

*Primary Examiner* — Sanjay Cattungal
(74) *Attorney, Agent, or Firm* — Williams Mullen

(57) ABSTRACT

A system for the measurement of radiation emitted from an in-vivo administered radioactive analyte. The system employs a sensor having a scintillation material to convert gamma radiation to visible light, which enables embodiments of the sensor to be ex vivo. A light detector converts the visible light to an electrical signal. This signal is amplified and is processed to measure the captured radiation. Temperature of the sensor may be recorded along with this radiation measurement for temperature compensation of ex vivo embodiments. The sensor enables collection of sufficient data to support separate application to predictive models, background comparisons, or change analysis.

34 Claims, 26 Drawing Sheets

(56) References Cited

U.S. PATENT DOCUMENTS

| | | |
|---|---|---|
| 2003/0189657 A1 | 10/2003 | Hammadou |
| 2005/0143927 A1 | 6/2005 | Cammia et al. |
| 2005/0287065 A1 | 12/2005 | Suddarth et al. |
| 2006/0076523 A1 | 4/2006 | Higashiisogawa et al. |
| 2009/0150315 A1 | 6/2009 | Wirtz et al. |
| 2009/0226915 A1 | 9/2009 | Guyon |
| 2010/0010343 A1* | 1/2010 | Daghighian et al. .......... 600/436 |
| 2010/0198061 A9* | 8/2010 | Daghighian et al. .......... 600/436 |
| 2010/0268078 A1 | 10/2010 | Scarantino et al. |
| 2011/0196234 A1* | 8/2011 | Buono et al. .................. 600/436 |
| 2011/0301863 A1 | 12/2011 | Auribault et al. |
| 2014/0018675 A1* | 1/2014 | Keppel et al. ................. 600/436 |

OTHER PUBLICATIONS

Basak, Abhishek, Low-Power Implantable Ultrasound Imager for Online Monitoring of Tumor Growth, 33rd Annual Intl Conference of the IEEE EMBS, Boston, MA., Aug. 30-Sep. 3, 2011, pp. 2858-2861.

International Search report dated Feb. 19, 2014.

* cited by examiner

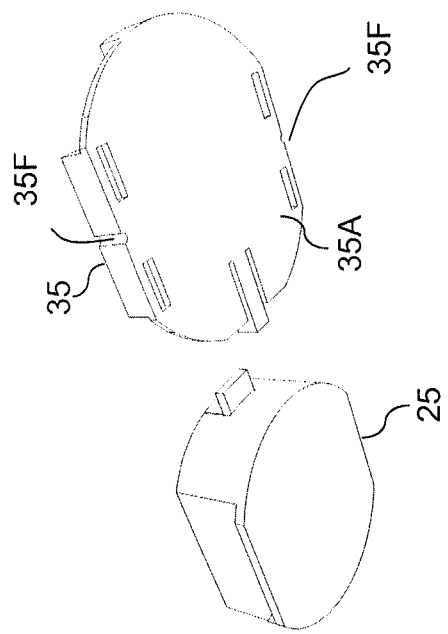
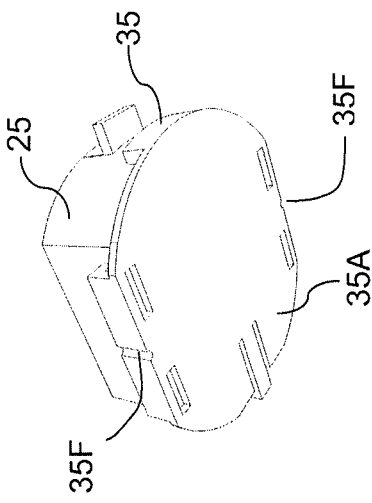
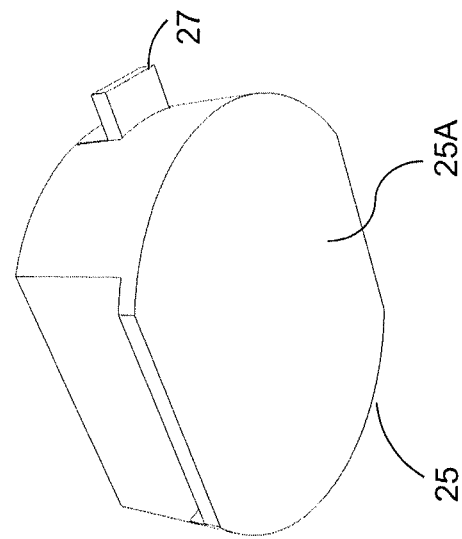
FIG. 4B
FIG. 4C
FIG. 4A

SYSTEM FOR THE DETECTION OF GAMMA RADIATION FROM A RADIOACTIVE ANALYTE

RELATED APPLICATIONS

This application claims the benefit of U.S. Provisional Application No. 61/653,014, filed on May 30, 2012, which is hereby incorporated in its entirety.

STATEMENT REGARDING GOVERNMENT SUPPORT

None.

FIELD OF INVENTION

The present invention relates to measurement and prediction of biological processes, and more particularly to a system and method for using localized radio-labeled tracer temporal uptake to measure and predict biological processes.

BACKGROUND

Oncologists are interested in knowing if the prescribed cancer therapy is having the intended effect, but the tools available to them today to assess a tumor's response to treatment are not very helpful. Palpating the tumor is easy and inexpensive, but it is limited to tumors close to the surface, relies on a physician's memory and notes, and primarily measures size, a trailing indicator of therapy effectiveness. Size reduction only occurs after therapy kills tumor cells and the body's natural processes eliminate the dead cells. Imaging tools (CT, MRI, x-ray) are precise for tumors both close to the surface and in deep tissue, but again primarily measure size, a trailing indicator. Molecular imaging (PET/CT scan) measures both leading and trailing indicators (i.e., metabolism or proliferation, and size) of tumors by capturing positrons emitted from injected radioactive tracers. PET/CT scans are routinely used for pre-therapy staging of cancer. Comparisons of the semi-quantitative Standardized Uptake Values (SUVs) derived from baseline and follow-up PET/CT scans are currently the best available indicator for therapy effectiveness. However, due to the high cost of PET/CT scans, payers limit reimbursement to just a pre-therapy staging scan, except for lymphoma patients. So, oncologists today are left with no timely, cost-effective, and fast way to evaluate the therapy they deliver.

Attempts have been made to image the uptake of radio-labeled tracers using a Positron Emission Tomographic (PET) machine where a small portion of the body is imaged repeatedly. This approach is known as Dynamic PET, and is too slow and costly to be of widespread clinical adoption.

In light of the problems associated with current tumor measurement and prediction systems, it is an object of the present invention to provide an easier, less costly, and more efficient system and method for measuring and predicting the status and/or changes in biological processes.

SUMMARY

Disclosed is a system for measuring radio-labeled tracer uptake into a biological system in an easy, quick and relatively inexpensive manner along with requiring less radio-labeled tracer and inflicting less discomfort on the patient. Physicians are better able to make treatment decisions in a cost effective and efficient manner. Although embodiments of the system of the present invention described below relate to measuring and predicting changes in a tumor, for example, embodiments of the system of the present invention can be used to measure processes in nearly any biological system. For example, the system can be used for non-tumor brain scans, etc.

Any number of embodiments of the present invention provide a hardware and software system which is used to gather real-time measurements of radio-labeled tracer uptake in a biological process, for example a tumor. Sensors measure the localized uptake of a radio-labeled tracer which is injected into the patient or subject. In an embodiment, for example, sensors can be placed in the following locations: (a) directly over the tumor; (b) on the upper right arm, approximately 10 cm above the antecubital fossa; (c) on the upper left arm, approximately 10 cm above the antecubital fossa; and (d) over another area of interest.

In any number of embodiments, measurements taken at the sensors can be performed quickly and repeated often. The system of the present invention reduces the amount of expensive radioactive tracer necessary for accurate measurement readings verse the amount required for other measurement methods and eliminates the necessity of using a large PET scanner or similar piece of equipment for follow-up scans (PET/CT scanners may continue to be used to stage diagnosed cancers and to check the subject for metastasis). Measurements made by the present approach reveal the kinetics of the tumor. Biological differences in tumors cause different amounts of radioactive analyte to be consumed locally as compared to normal tissue. The present invention senses and quantifies this consumption, then processes the data into an easy-to-read graph for the oncologist within minutes. Comparing graphs over time—baseline versus subsequent scans—shows the changes in tumor parameters. Changes in biological parameters within the tumor can give the physician insight into whether treatment is working or not. Additionally, the present invention can use predictive algorithms to predict likely changes in biological parameters based on one measurement scan, which speeds the time required to know the likely effectiveness of treatment.

In any number of embodiments, the system can comprise: (i) one or more Measurement Sensors; (ii) a Measurement Control Device; (iii) Computer Software capable of executing measurement and prediction data; and (iv) Database Server Control Software.

In one embodiment, a Measurement Sensor can be a device comprising a scintillation material; a light detector; and an embedded processor with associated embedded software, memory, logic and other circuitry on a printed circuit board. In an embodiment, for example, the sensor's electronics are enclosed in a light-proof enclosure and there can be a multi-conductor cable to enable data communications. Mechanical design of the housing can be used to accurately control the placement of the scintillation material.

In one embodiment, a measurement control device can be, for example, a device comprising a display screen, a keypad and data communications connectors. The control device can further comprise an embedded processor with associated embedded software, memory, a real-time clock, and other associated logic and circuitry on a printed circuit board. In an embodiment, there can be multiple data communications connectors to enable the attachment of multiple measurement sensors. Another embodiment of the control device also includes a data communications connector to enable connection to a computer.

In any number of embodiments, the specialized computer software used in the system of the present invention is capable of: (1) performing diagnostic tests on the measurement control device; (2) transferring measurement data from the measurement control device and saving it to a record file; (3) gathering ancillary test data from the user or other sources (radiation dose administered, patient weight, patient blood-glucose readings, PET scan data, etc.) and including it in the data record file; and (4) transferring the data record file to the database server control software.

In any number of embodiments, the database server control software can be capable of accepting incoming data record files from the computer software and applying one or more Algorithms to the data received. Simple algorithms include, but are not limited to smoothing and/or noise reduction, radioactive decay correction, amplitude correction based on control signals, etc. More complex algorithms can be machine learning algorithms such as Classification Decision Trees, Rule Learning, Inductive Logic, Bayesian Networks, etc. Measurement data can be stored in a central database while the Algorithm output can be used to generate reports for the user. These reports can indicate estimated parameters or even estimated future parameters of a tumor or other biological process.

BRIEF DESCRIPTION OF THE DRAWINGS

FIGS. 4A-4C illustrate optional aspects of the system.

DETAILED DESCRIPTION OF THE PREFERRED EMBODIMENTS

Figure 1:
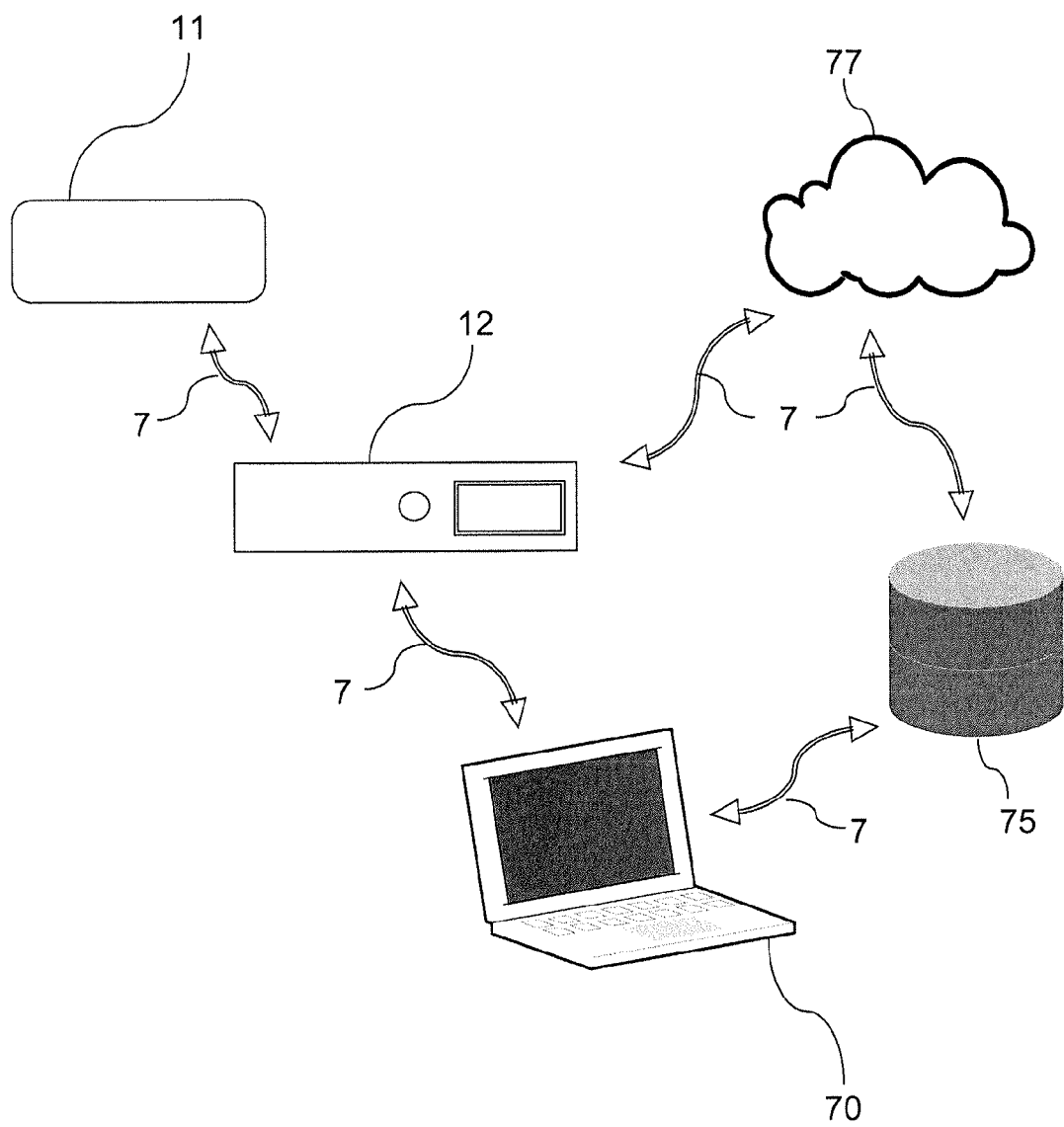
FIG. 1 is an illustration of an overview of the system.

Disclosed is a system for measuring gamma radiation emitted from an in-vivo administered radioactive analyte. If repeated measurements are made, these measurements will show changes in the measured radiation over time. These repeated measurements can be used to calculate parameters related to the data. The repeated measurements can also be used as inputs to predictive algorithms to predict future parameters.

The system is a hardware and software system which can be used to gather real-time measurements of radio-labeled tracer uptake in a biological process, for example a tumor. It employs a sensor for the detection of gamma radiation emitted by a subject from a systemic administration of a radioactive analyte that generally decays in vivo by positron emission. A sensor for gamma ray detection enables the use of ex vivo or in-vivo devices, while ex-vivo devices can be safer for the subject due to their less intrusive design. Elements and capabilities of embodiments of the system are described in more detail below.

The system 10 employs a scintillation material 20 that converts gamma radiation to visible light. A light detector 21 then converts the visible light to an electrical signal. This signal is amplified and is processed to measure the captured radiation. In ex vivo embodiments, temperature of the sensor is recorded along with this radiation measurement, and this data may be collected by a measurement controller or control device 12 into a record file 80. This record file 80, along with others like it from previous measurement sessions, may be used as inputs to calculate data parameters or as input to predictive models to predict data parameters. Record file 80 is intended simply to denote a collection of data by subject 5, and such other criteria applicable to the circumstances, such as tumor location, condition, time of test, etc.

An embodiment of system 10 shown in FIG. 1 is directed to the detection of gamma radiation emitted by a subject 5 (not shown) from systemic administration of a radioactive analyte that decays in vivo by positron emission. The system 10 may include one or more measurement sensors 11 (or device for the detection of radiation), a measurement control device 12, an optional processing station 70, and optional database 75. Communication links 7 may be wired or wireless, depending on the application, and may extend data reporting or other communication to networks or the internet 77.

Figure 2:
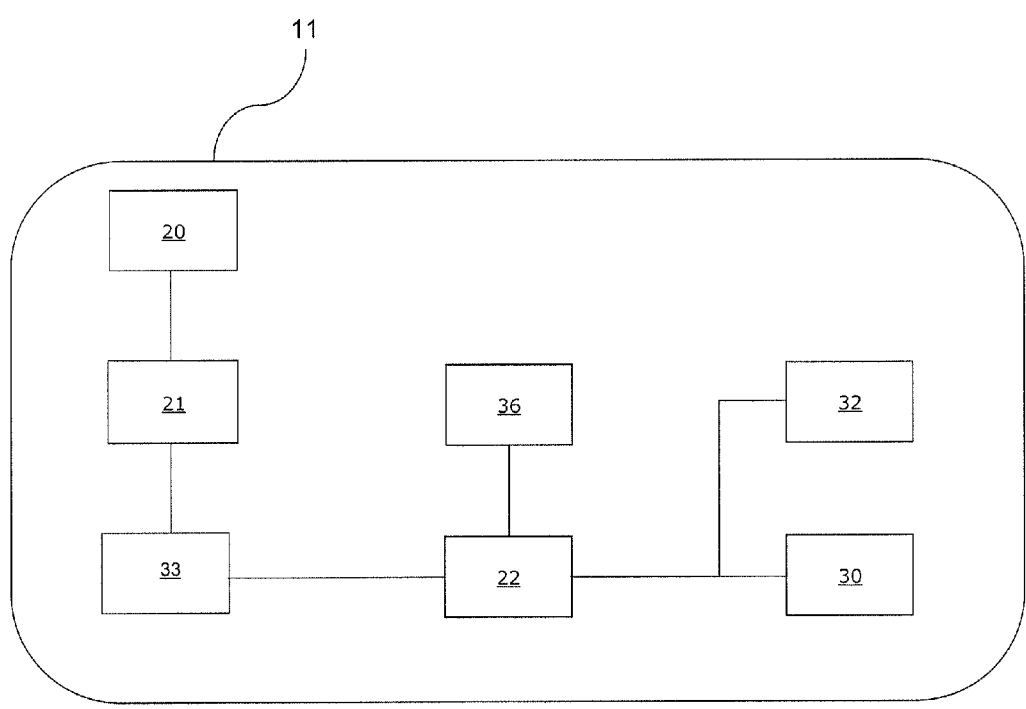
FIG. 2 is a schematic of a measurement sensor of an embodiment of the system.

With reference to FIG. 2, measurement sensor 11 may have a sensor housing 25 (not shown), a scintillation material 20, a light detector 21, a temperature sensor 36, a signal amplifier 33, a sensor processor 22, a non-transient sensor memory 30, and a sensor power supply 32. Light detector 21, temperature sensor 36, signal amplifier 33, sensor processor 22, sensor memory 30, and sensor power supply 32 may be in operable communication, whether by wiring, circuit board tracing, etc.

Figure 3:
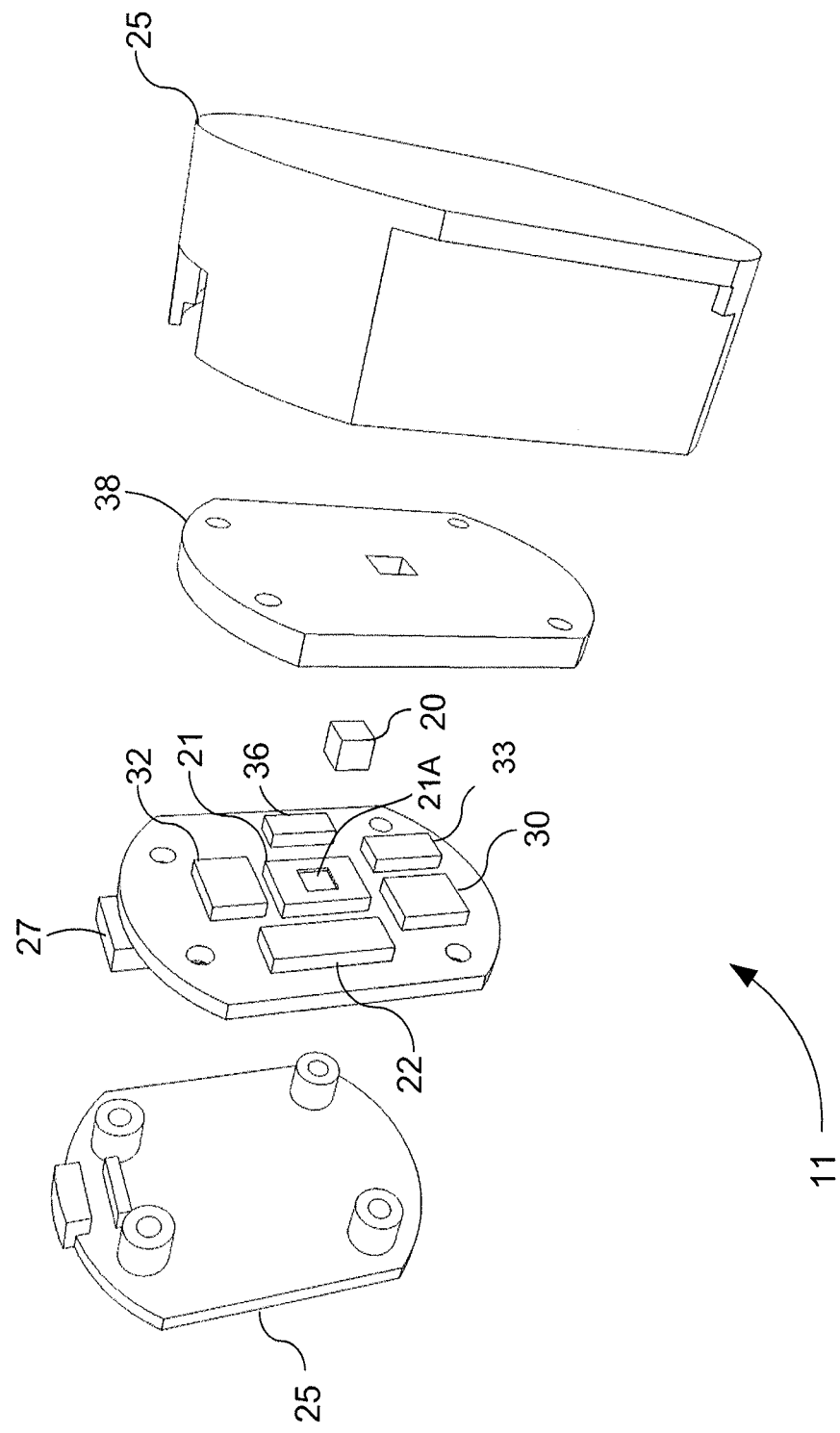
FIG. 3 is shows an embodiment of a measurement sensor of the system.

As shown in the exploded illustration of FIG. 3, scintillation material 20 and light detector 21 may be disposed or located within housing 25 for use, depending on the application. Sensor housing 25 may be fabricated of metal (e.g., nickel, copper, brass, bronze, steel, aluminum, nickel-silver, beryllium-copper, etc.) or plastic (PE, PP, PS, PVC, ABS, etc.), Such sensor housing 25 may optionally be light proof, so as to protect scintillation material 20 and light detector 21 from ambient or surrounding light. Optionally, sensor housing 25 may define an outer surface and comprises a lightproof coating on the outer surface. Sensor housing 25 may also protect such internal components from environmental degradation, such as the exposure of scintillation material 20 to elevated humidity. Sensor housing 25 may include or incorporate a shielding mask 38 or shield for the radiation of concern, such as the ex vivo detection of gamma radiation. Shielding mask 38 may be fabricated from materials such as iridium, platinum, tungsten, gold, palladium, lead, silver, molybdenum, copper, nickel, bronze, brass, iron, steel, zinc, titanium, and aluminum.

In use, and as shown in FIGS. 4A-C, embodiments of sensor housing 25 may include an adhesive 25A adapted for the removable attachment of the housing to the skin of the subject 5. Optionally, system 10 may include a measurement sensor carrier 35 adapted to removably engage with the measurement sensor 11. The measurement sensor carrier 35 may define a carrier surface with a portion of which may comprise an adhesive 35A adapted for removable attachment of the measurement sensor carrier 35 to the skin of a subject 5 (not shown). Optionally, measurement sensor carrier 35 includes or defines one or more alignment features 35F that permit the repeated alignment of the measurement sensor carrier 35 to the subject. For example in the embodiment as shown, measurement sensor carrier 35 defines two features 35F that could be used to align a marker to make a mark or stain dot on the skin of subject 5. For a repeated trial, measurement sensor carrier 35 might be placed in a position so that alignment features 35F might align with the marks on the skin of subject 5, ensuring that measurement sensor 11 is in the proper location. Measurement feature 35F may include a variety of approaches depending on the application, such as pads for temporary tattoo markings, peripheral outline ridges, guides permitting the marking of orientation axes, etc.

Sensor power supply 32, or the other power supplies discussed herein, may be a battery, a hardwire power connection, transformer, or some form or source of power generation. In some embodiments, sensor power supply 32 in particular, may be a microelectromechanical machine adapted to generate electricity from subject 5, possibly employing the motion of subject 5, or blood pressure, etc.

Scintillation material 20 may be placed within a gamma radiation flux, with scintillation material 20 being adapted to receive a level of gamma radiation from the in vivo radioactive analyte and to emit photons representative of or corresponding to the gamma radiation level. Light detector 21 may be juxtaposed, located, or generally disposed with respect to the scintillation material 20 so as to be adapted to receive and convert the multiplied photons into signal data representative of the level of gamma radiation received. It is contemplated that some applications may include mechanisms or structure for directing light from scintillation material 20 to light detector 21, such as fiber optics, prisms, reflectors, etc. Optionally, and as shown in FIG. 3, light detector 21 may have an active area 21A sensitive or receptive to light as described herein, and the scintillation material 20 may be configured and sized to substantially match the active area, which may improve efficiency and reduce the effect of stray light or background signals.

The scintillation material 20 may be selected for or adapted to the radiation detection application. In some embodiments for gamma radiation, scintillation material 20 may be selected from a group consisting of bismuth germanate, gadolinium oxyorthosilicate, cerium-doped lutetium oxyorthosilicate, cerium-doped yttrium oxyorthosilicate, sodium iodide, thallium-doped sodium iodide, polyvinyltoluene, and cadmium zinc telluride.

Measurement sensors 11 may include a signal amplifier 33 that is adapted to amplify the signal data, a sensor memory 30 including a measurement sensor identifier 16 (FIG. 6), and at least one sensor output port 27 for communication or output of the amplified signal data. Depending on the mode of communication desired, sensor output port 27 may be any of a variety of ports, such as electrical jack, computer communication (e.g., CAT-5), optical, infrared, radio transmitter, etc.

Figure 5A:
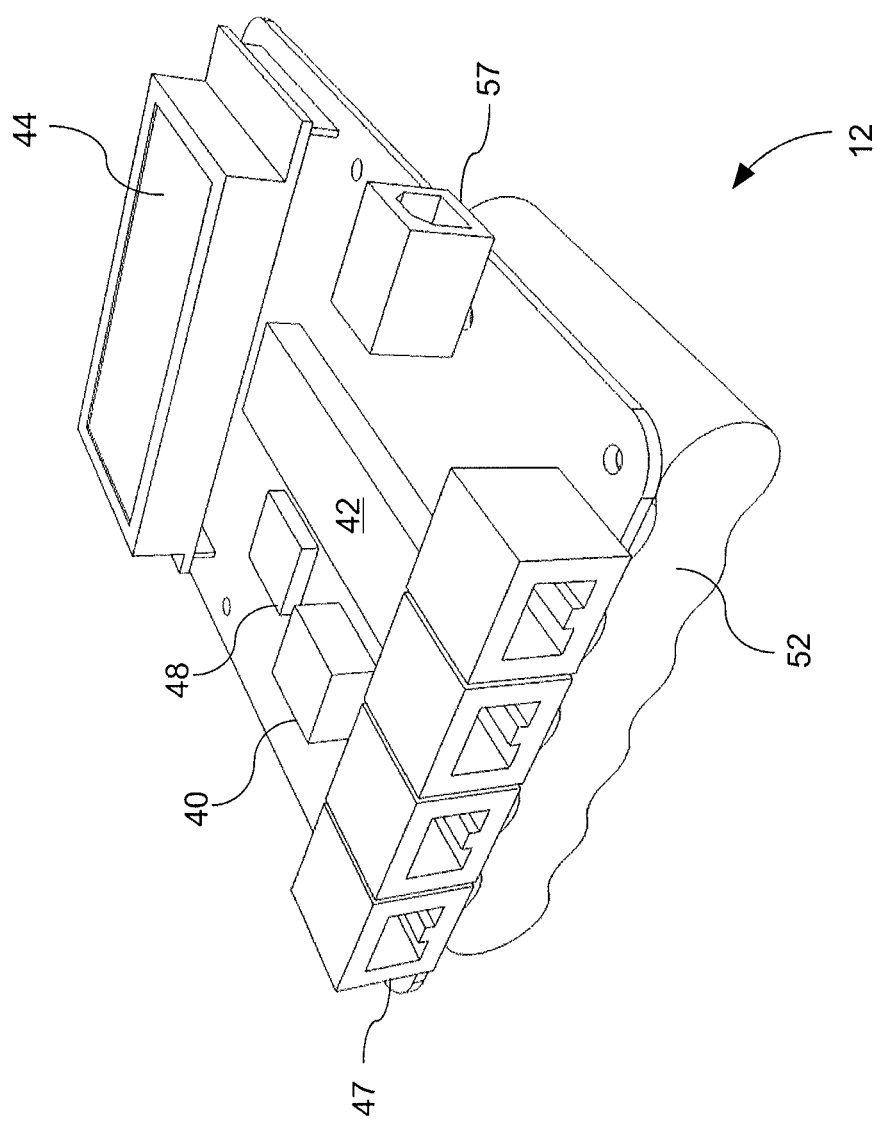
FIGS. 5A-5C illustrate embodiments of measurement control devices.
Figure 5B:
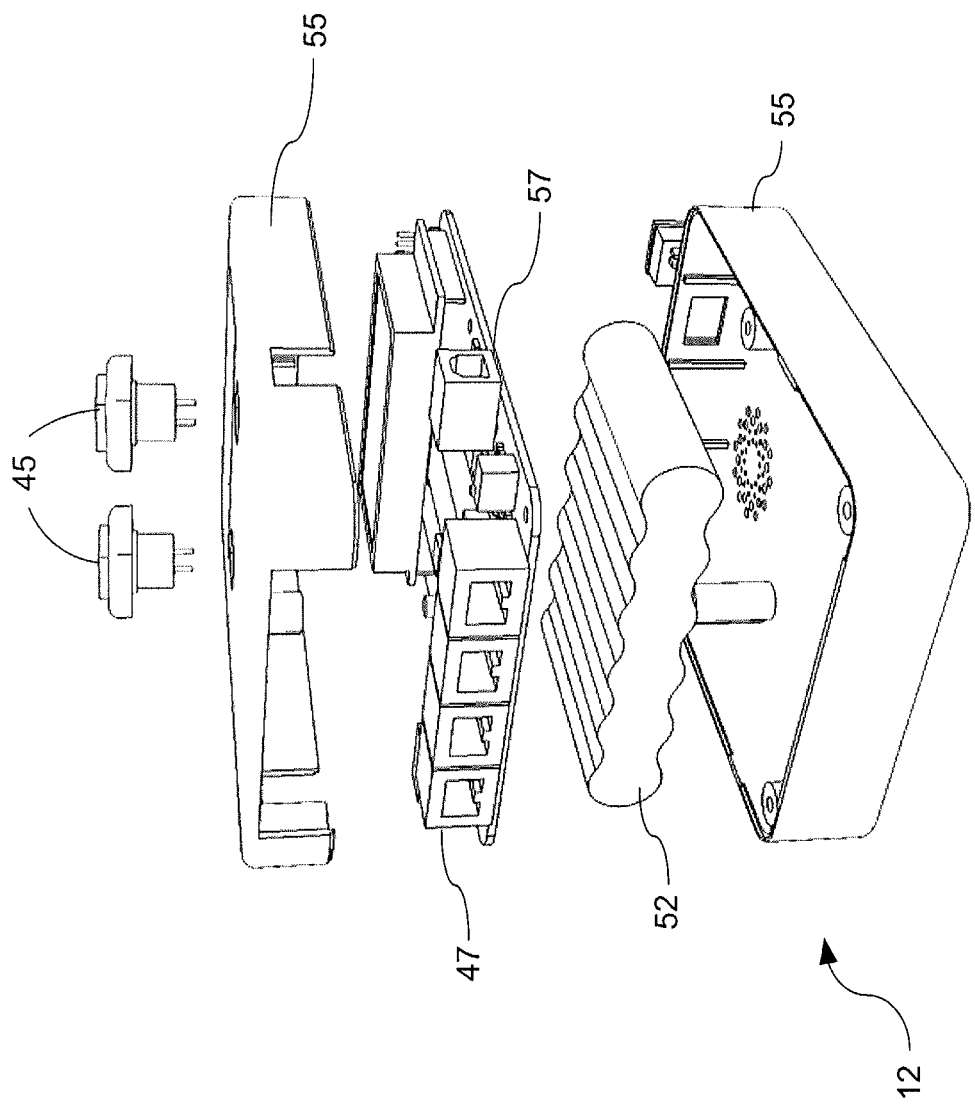
Figure 5C:
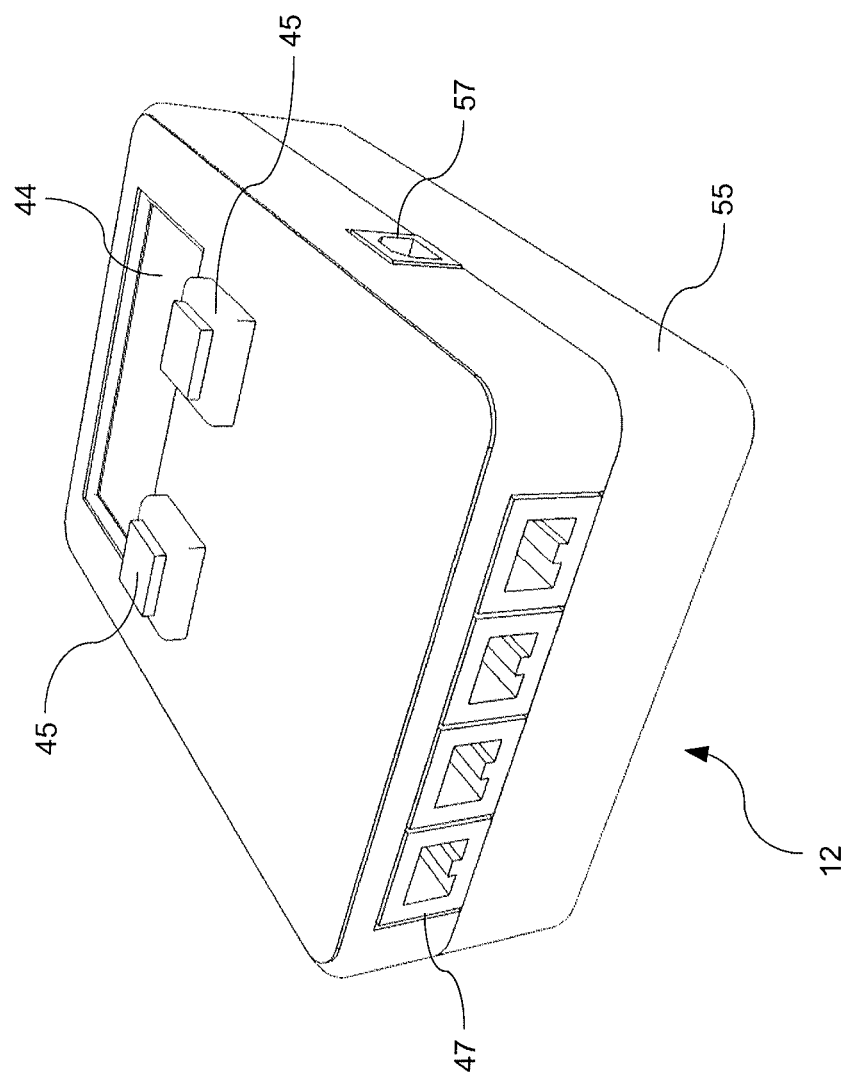

In reference to the examples in FIGS. 5A-C, the system 10 may include a controller or measurement control device 12 having a control processor 42, a non-transient control memory 40, a control power supply 52, and a clock 48, all in operable communication, whether by wiring, circuit board tracing, etc. The measurement control device 12 may include a control input port 47 operably engaged with the sensor output port 27 (not shown) and adapted to receive amplified signal data from the measurement sensor 11. Operable engagement may include wired or wireless communication, in any of a variety of communication protocols. For example, control input port 47 may be operably engaged with the sensor output port 27 by cable (e.g., multiconductor cable 24), or by wireless communication. In addition to amplified signal data, it may be desirable to communicate other data or information from measurement sensor 11 to measurement control device 12, such as operating parameters, power storage, equipment status, or other sensor data. Optionally, measurement control device 12 may include a display 44 and data entry device 45, such as a touch screen, or other input/output structure.

The control memory 40 may, among other things, include control computer program code 56 (FIG. 6) executable by the control processor 42. Control computer program code 56, for example, may include a first module 61 for implementing measurement functions and a second module 62 for data management. For example, the first module 61 may be adapted to receive a previously assigned measurement sensor identifier 16 (discussed below), the signal data, and a subject identifier and to associate the signal data, sensor identifier, and measurement sensor identifier 16 in a record file 80 format. The second module 62 may be adapted to receive the signal data of a record file 80 from the first module 61 and to transmit the compensated signal data to a desired storage. Such storage may be local memory (e.g., sensor or control), external memory, a remote computer memory, networked memory (wireless or wired), or memory accessed via the internet.

The system 10 may include a temperature compensator 50 coupled with the temperature sensor 36, the temperature sensor 36 adapted to measure an ambient temperature within the system 10 adapted to communicate the ambient temperature to the temperature compensator 50. In this way, the temperature compensator 50 may be adapted to generate a temperature correction factor based on comparison of the ambient temperature to a reference temperature. As discussed below, components within measurement sensor 11 may be temperature sensitive. The temperature compensator 50 may also be adapted to apply the temperature correction factor to the signal data to produce temperature compensated signal data. Temperature compensation may not be required for embodiments directed to in vivo sensing.

Figure 7:
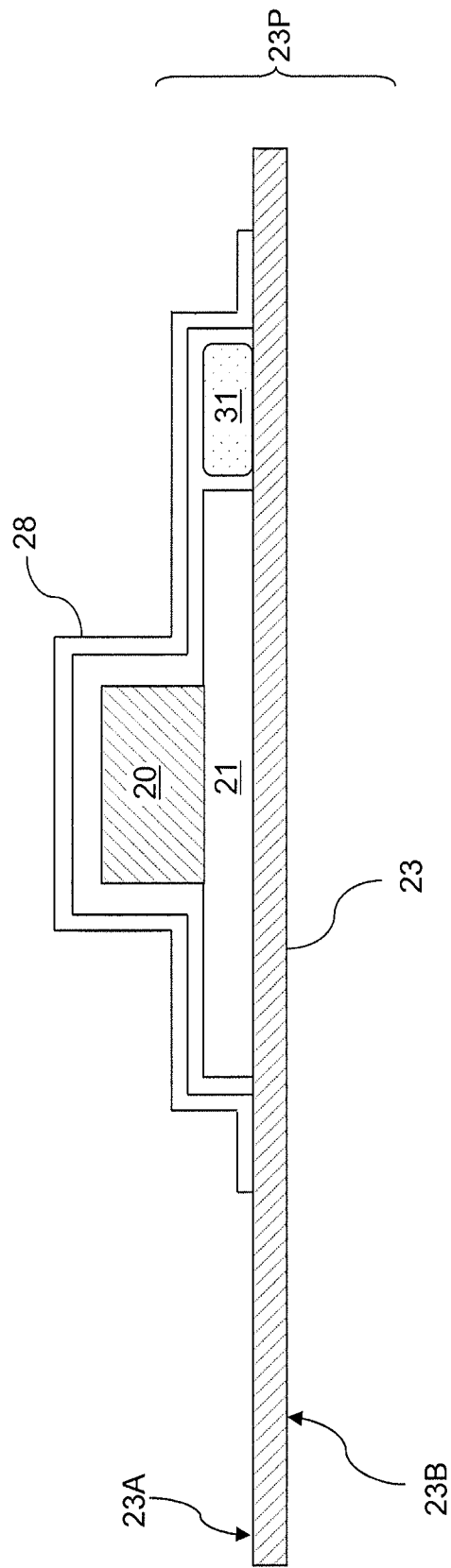
FIG. 7 shows an embodiment of a printed circuit board and light shield.
Figure 8B:
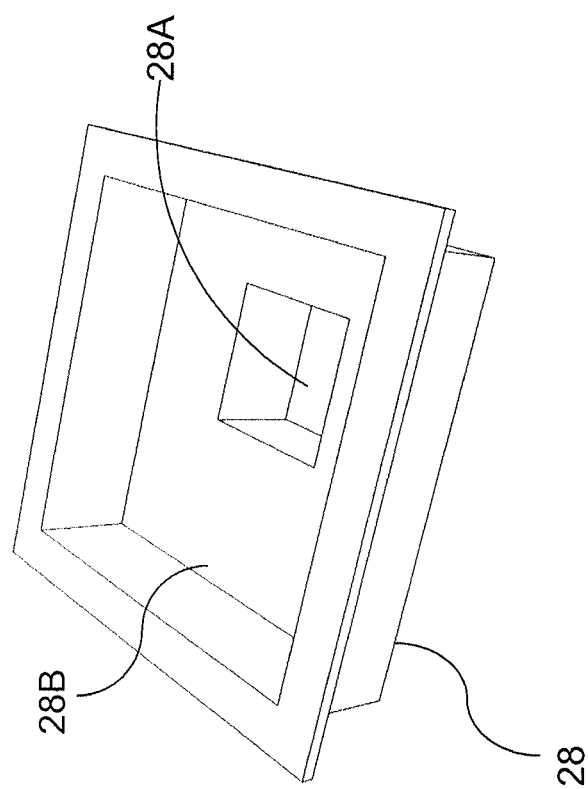
FIGS. 8A-8B illustrate an embodiment of a light shield.
Figure 8A:
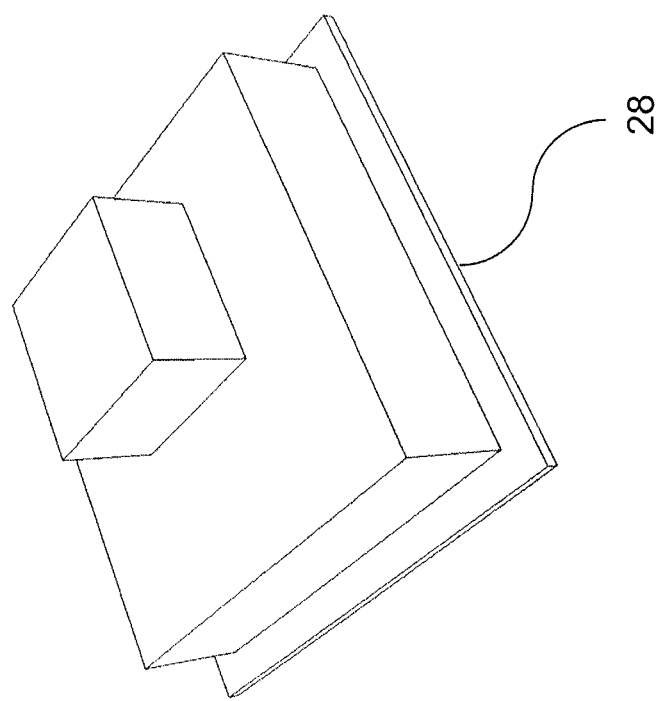

Optionally, as shown in FIGS. 7-8, embodiments of measurement sensor 11 may include an internal disposed light shield 28. Such an embodiment may include a printed circuit board assembly 23P having a board 23 defining a plane with a first surface 23A and an opposing second surface 23B. Light shield 28 may be adapted for mounting onto the first surface 23A of the board 23, thereby shielding the scintillation material 20 and light detector 21 from ambient light. The scintillation material 20 and light detector 21 may be ensconced in or surrounded by light shield 28. For example, given that the scintillation material 20 has a first width parallel with the plane and the light detector 21 has a second width parallel with the plane, then light shield 28 may define a first cavity 28A with a third width equal or greater than the first width such that the first cavity 28A is adapted to receive the scintillation material 20, and the light shield 28 may also define a second cavity 28B with a fourth width equal or greater than the second width such that the second cavity 28B is adapted to receive the light detector 21. First and second cavities 28A, 28B may be in communication and in such proximal relation that the light shield 28 optically aligns the scintillation material 20 to the light detector 21 when the scintillation material 20 is received by the first cavity 28A and the light detector 21 is received by the second cavity 28B. These components may be operably engaged with the printed circuit board assembly 23P when mounted. For purposes herein, the term "width" is intended to connote an effective width that permits the nesting described, and not any particular required cross sectional shape. In other words, the term "width" is intended to permit the reception of the components as described, and not to limit cross section shape of those components beyond their interrelation.

Such a light shield 28 may be made from materials selected from a group of metals (e.g., copper, brass, bronze, steel, aluminum, nickel-silver, beryllium copper, silver, gold, nickel), or plastic (e.g., ABS, Acetal, Acrylic, Fluoroplastic, Polycarbonate, Nylon, PVC, Polypropylene, Polystyrene, Polyethylene ABS, Acetal, Acrylic, Fluoroplastic, Polycarbonate, Nylon, PVC, Polypropylene, Polystyrene, Polyethylene). Optionally, the light shield 28 may be made from one material and plated or coated in another, to enhance its ability to be soldered or mounted on printed circuit board assembly 23P.

If made from metal or metal clad or plated plastic, the light shield 28 may be fixed into place on printed circuit board assembly 23P as a surface-mount-component using either leaded or lead-free solder, or as a through-hole-component using portions of the light shield 28 that protruded through holes in the circuit board, the holes then filled with solder. If made from plastic, the light shield 28 may be fixed into place on the printed circuit board assembly 23P as a snap-on part with portions of the shield that protrude through holes in the printed circuit board assembly 23P that spring into position and resist reversing out of the holes, as a swage-on part with portions of the shield that protrude through such holes and that are then melted or swaged to prevent them from reversing out of the holes.

Optionally, light shield 28 may have one or more through-holes in it to allow pressure to equalize during assembly or to allow for out-gassing during assembly. Such holes may then be covered, possibly with light-proof foil tape, after assembly to complete the light-proof nature of the shield.

As shown in FIG. 7, light shield 28 may also enclose a light emitter 31 (e.g., LED, light bulb, laser diode) such that the light emitter could be used to generate pulses of light within the enclosure of the light shield 28 to test the light detector 21. Thus, system 10 may include a light emitter 31 in operable communication with the sensor power supply 22, the light emitter 31 disposed within first or second cavity 28A, 28B (or other proximal cavity), such that the light shield 28 is adapted to receive the light emitter 31 in a location that is proximal to the light detector 21.

In some embodiments, the control computer program code 56 further comprises a third module 63 adapted to receive stored data of a record file from the second module 62. The third module 63 may apply such stored data to a predictive model to generate predictive data values over a desired period for such record file as a predictive outcome, and to transmit such predictive outcome to a desired storage. In other embodiments, the third module 63 may to apply such stored data to calculate changes in the compensated signal data over a desired period, and to transmit such changes to a desired storage. In other embodiments, the third module 63 may to apply such stored data to calculate changes in the compensated signal data from background data over a desired period, and to transmit such changes to a desired storage. Such background data may be drawn from a second measurement sensor 11, a previously calculated background radiation level, or a separate radiation sensor, depending on the application.

Figure 9:
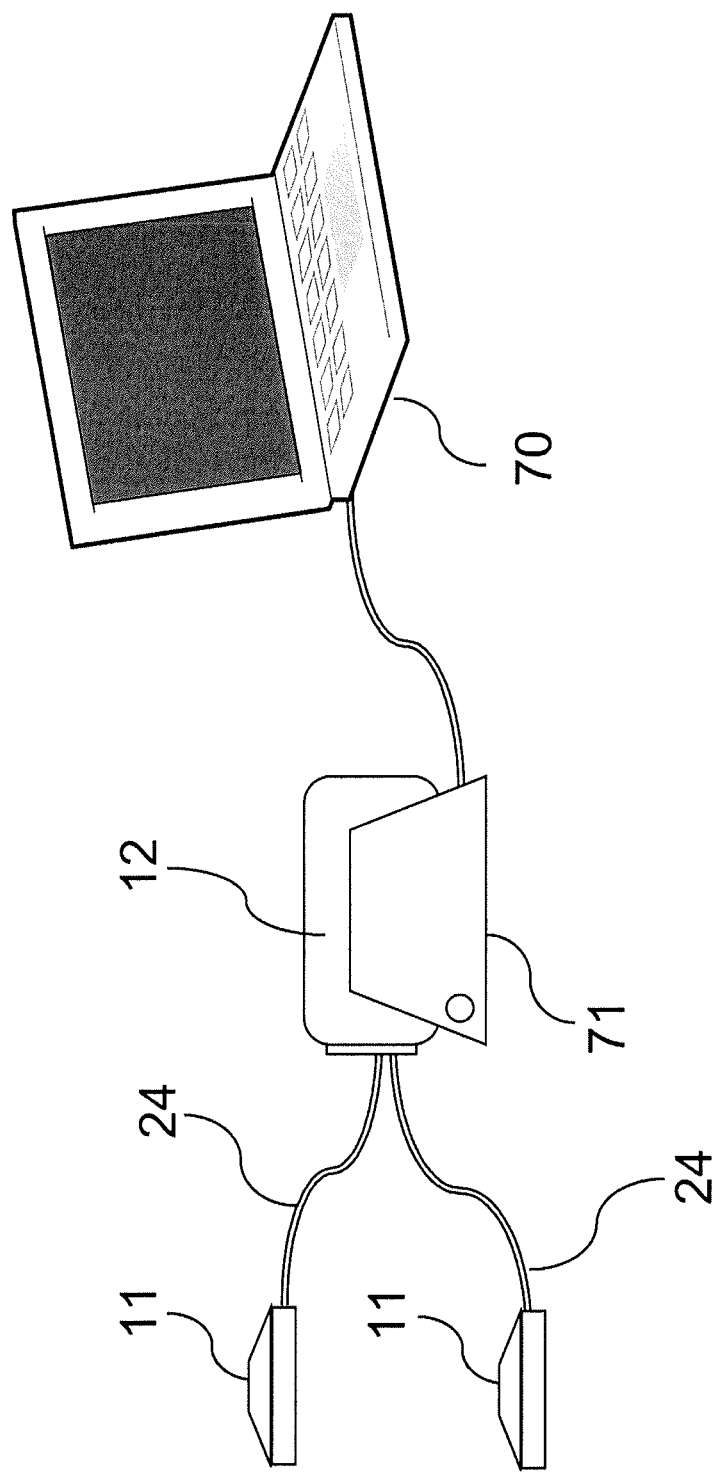
FIG. 9 shows an aspect of embodiments of the system.

In some embodiments, system 10 may include a processing station 70 (FIGS. 1 & 9). Processing station 70 may be a computer in communication with measurement control device 12. Embodiments of processing station 70 may include a station processor, a non-transient station memory, and a station power supply; the station processor, station memory, and station power supply are in operable communication. The processing station 70 may have a station input port operably engaged with the control output port and adapted to receive data from the measurement control device 12. In some embodiments, the role of measurement control device 12 and station 70 may be merged.

Similar to measurement control device 12, the processing station 70 may include station computer program code 76 executable by the station processor, the station computer program code including a third module 63 adapted to receive stored data of a record file from the second module 62, to apply such stored data to a predictive model to generate predictive data values over a desired period for such record file as a predictive outcome.

Optionally, processing station 70 may include a docking device 71 for the measurement control device 12. The docking device 71 may be in operable communication with the station processor. Docking device 71 could be adapted to receive the measurement control device in the form of a holder, retainer, charger, or cradle. When measurement control device 12 is docked, the docking device 71 may provide an electrical connector that engages with measurement control device 12 for data communication and power exchange.

In some embodiments, predictive model may be a classification machine learning model. In other embodiments, predictive model may be an unsupervised cluster analysis. Such an unsupervised cluster analysis, or other predictive model, may be adapted to predicting future outcome, predicting an effect of tumor treatment, and predicting metastasis.

Some embodiments may involve multiple measurement sensors 11. For example, a system 10 may include a first and second measurement sensor 11, the first measurement sensor 11 adapted to the detection of test gamma radiation emitted by a subject from systemic administration of a radioactive analyte that decays in vivo by positron emission proximate to a test area. The second measurement sensor 11 may be adapted to the detection of background gamma radiation emitted by a subject from systemic administration of a radioactive analyte that decays in vivo by positron emission proximate to a background area. Depending on the application, the control computer program code 56 or station computer code 76 may further include a fourth module 64 adapted to receive stored data of a record file from the second module 62 including data from the first and second measurement sensors 11 and to subtract signal data from the second measurement sensor 11 from signal data from the first measurement sensor 11. In other applications, the fourth module 64 may be adapted to receive stored data of a record file from the second module 62 including data from the first and second measurement sensors 11, and to subtract signal data from the second measurement sensor 11 from signal data from the first measurement sensor 11. Such embodiments may permit the subtraction of background radiation from sensor data.

In some embodiments, the signal data may be a plurality of pulses at a pulse frequency over time. The first module 61 may be adapted to communicate a sampling frequency instruction to the sensor processor 22, the sampling frequency instruction being a function of the pulse frequency of the signal data. In some embodiments, the first module 61 is adapted to communicate an increasing sampling frequency instruction upon an increase in pulse frequency.

An aspect of present approach is a sensor or device for the detection of radiation, the device comprising a measurement sensor 11 with a housing 25, a scintillation material 20, a light detector 21, a light shield 28, a temperature sensor 36, a signal amplifier 33, a sensor processor 22, a non-transient sensor memory 30, and a sensor power supply 32. Light detector 21, temperature sensor 36, signal amplifier 33, sensor processor 22, sensor memory 30, and sensor power supply 32 may be in operable communication by a printed circuit board assembly 23P. Printed circuit board assembly 23P may have a board 23 defining a plane having a first surface 23A and an opposing second surface 23B. Light shield 28 may be adapted for mounting onto the first surface 23A of the board 23B, thereby shielding the scintillation material 20 and light detector 21 from ambient light. The scintillation material 20 and light detector 21 may be ensconced in or surrounded by light shield 28. For example, given that the scintillation material 20 has a first width parallel with the plane and the light detector 21 has a second width parallel with the plane, then light shield 28 may define a first cavity 28A with a third width equal or greater than the first width such that the first cavity is adapted to receive the scintillation material 20, and the light shield 28 may also define a second cavity 28B with a fourth width equal or greater than the second width such that the second cavity 28B is adapted to receive the light detector 21. First and second cavities 28A, 28B may be in communication and in such proximal relation that the light shield 28 optically aligns the scintillation material 20 to the light detector 21 when the scintillation material 20 is received by the first cavity 28A and the light detector 21 is received by the second cavity 28B. These components may be operably engaged with the printed circuit board assembly 23P when mounted.

The scintillation material 20 and light detector 21 are thus disposed within the light shield 28 with the scintillation material 20 adapted to receive a level of gamma radiation and to emit photons representative of the gamma radiation level. Light detector 21 is disposed with respect to the scintillation material 20 so as to be adapted to receive and convert the multiplied photons into signal data representative of the level of radiation received.

As above, the signal amplifier 33 may be adapted to amplify the signal data, the sensor memory 30 including a measurement sensor identifier, the measurement sensor 11 having at least one sensor output port 27 for such amplified signal data. Optionally, the light shield 28 may be mounted to the first surface 23A of the board with solder. In some embodiments, light shield 28 is selected from a group consisting of metal: copper, brass, bronze, steel, aluminum, nickel-silver, beryllium copper, silver, gold, and nickel.

Figure 10A:
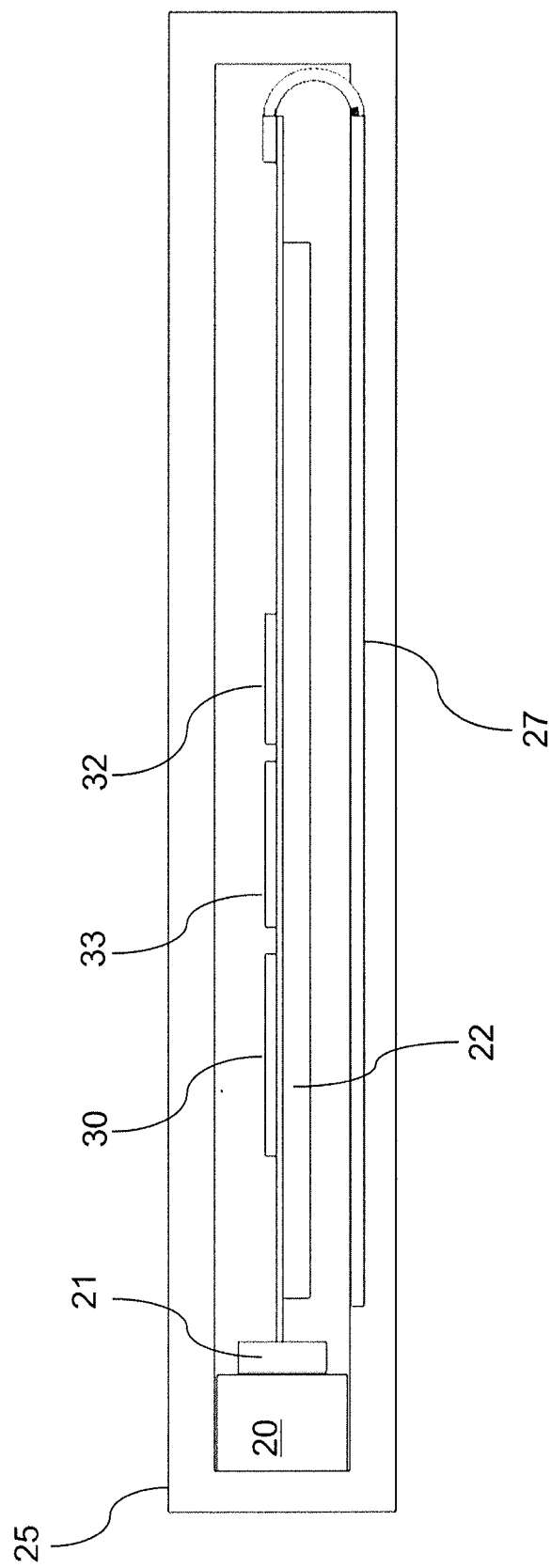
FIGS. 10A-10B show embodiments of a measurement sensor.
Figure 10B:
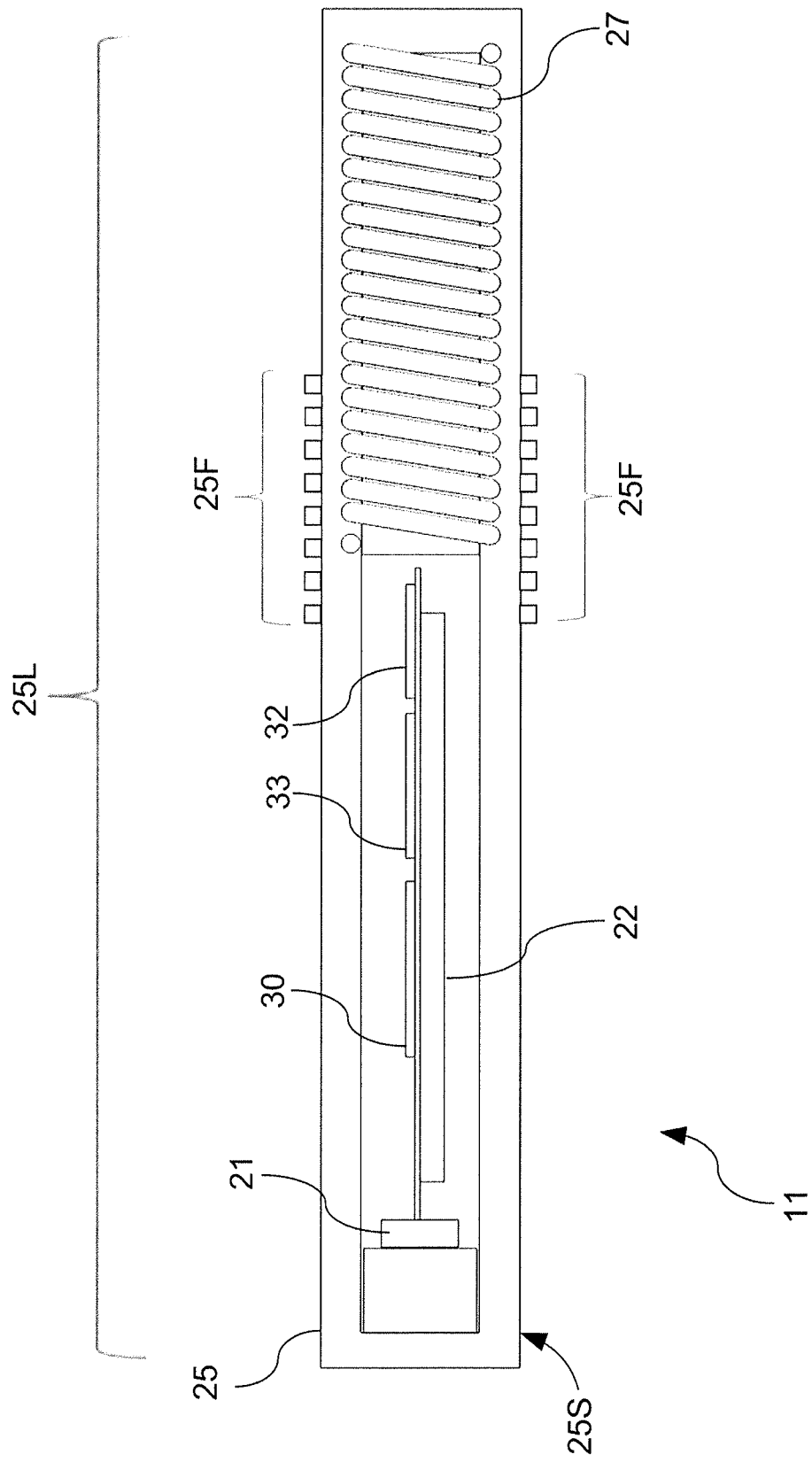

An aspect of some embodiments of system 10 for the detection of gamma radiation emitted by a subject is that at least one measurement sensor 11 may have a hermetically sealed sensor housing 25 of biocompatible material, a scintillation material 20, a light detector 21, a signal amplifier 33, a sensor processor 22, a non-transient sensor memory 30, and a sensor power supply 32, as shown in FIGS. 10A-10B. Light detector 21, signal amplifier 33, sensor processor 22, sensor memory 30, and sensor power supply 32 may be in operable communication, whether by direct wiring, circuit board tracing, wireless interaction, etc. Optionally, sensor housing 25 biocompatible material may be selected from a group consisting of glass, polyether ether ketone, and ultra-high-molecular-weight polyethylene appropriate for the application, such as meeting implantable standards for in vivo applications, for example. As a further option, sensor housing 25 may comprise an anchor 25F for securing an in vivo application in a desired location for testing or sensing.

Similar to as discussed above with reference to FIG. 3, light detector 21 may have an active area 21A and the scintillation material 20 may be configured to substantially match the active area 21A. The scintillation material 20 and light detector 21 may be disposed within the sensor housing 25 with the scintillation material 20 adapted to receive a level of gamma radiation from the in vivo radioactive analyte and to emit photons representative of the gamma radiation level, the light detector 21 disposed with respect to the scintillation material 20 so as to be adapted to receive and convert the multiplied photons into signal data representative of the level of gamma radiation received. The signal amplifier 33 may be adapted to amplify the signal data. The sensor memory 30 may include a measurement sensor identifier 16, the measurement sensor 11 having at least one wireless sensor output port 27 for such amplified signal data.

Such an embodiment of measurement sensor 11 may work with an ex vivo measurement control device 12 (not shown) having a control processor 42, a non-transient control memory 40, a control power supply 52, and a clock 48. Similar to as discussed above with reference to FIG. 5A-C, the control processor 42, control memory 40, control power supply 52, and clock 48 may be in operable communication, whether by direct wiring, circuit board tracing, or otherwise. The measurement control device 12 may have a wireless control input port 47 operably engaged with the wireless sensor output port 27 and adapted to receive amplified signal data from the measurement sensor 11.

Figure 6:
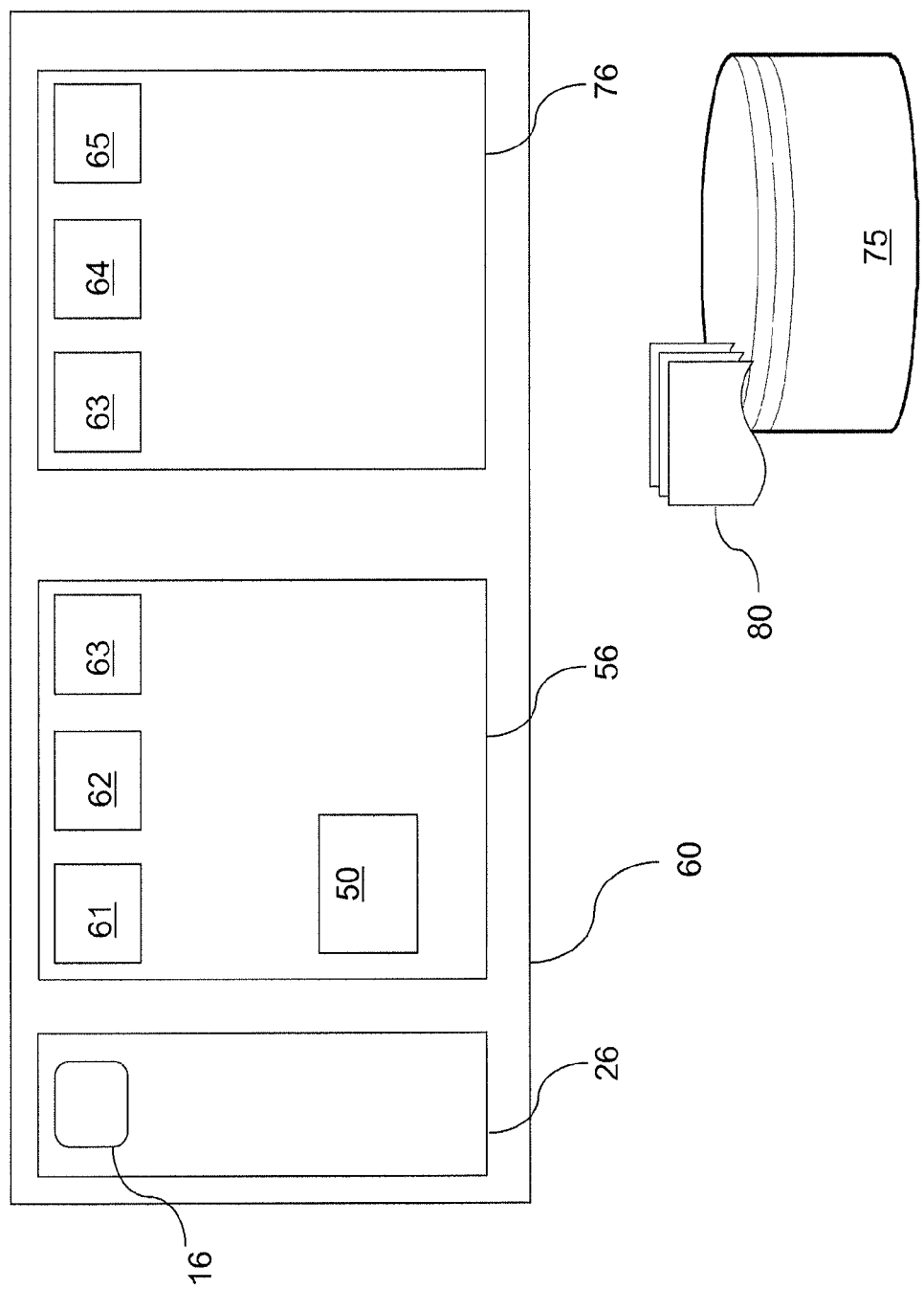
FIG. 6 illustrates an embodiment of computer program code of the system.

The control memory 40 may include control computer program code or software 56 executable by the control processor 42 (FIG. 6). Such control computer program code or software 56 may include a first module 61 for measurement and a second module 62 for data management. The first module 61 may be adapted to receive the measurement sensor identifier 16, the amplified signal data, and a subject identifier and to associate the signal data, sensor identifier 16, and measurement sensor identifier in a record file 80 format. The second module 62 may be adapted to receive the amplified signal data of a record file 80 from the first module 61 and to transmit the amplified signal data to a desired storage.

Optionally, the system 10 may include an in vivo measurement sensor 11 with a sensor housing 25 that is substantially tubular, which defines a sensor housing outer surface 25S and a sensor housing length 25L (FIG. 10B). In some such embodiments, the wireless sensor output port 27 may comprise an antenna running substantially along the length 25L of the sensor housing 25, along with supporting transmitters, etc. Substantially along the length simply means by general orientation or along a substantial portion (e.g., FIG. 10A), but it need not extend for the full length or be a straight antenna. It is contemplated, for example, that one embodiment of sensor output port 27 may comprise a coiled antenna oriented along a portion of length 25L, as shown in FIG. 10B. The anchor 25F may comprise at least one raised ring about a portion of a circumference of the sensor housing 25, which may or may not encircle the full circumference. The at least one raised ring or anchor 25F may disposed on the outer surface 25S and having a height from the outer surface of about 0.1-3.0 mm to anchor sensor housing 25 in place. Other embodiments of anchor 25F may include features such as adhesive, raised ridges, bumps, or eyelets, to minimize movement with respect to a patient or subject 5. Sensor housing 25 may also be provided in other general shapes, such as disks, lozenges, or egg-shapes.

In such an embodiment, optionally computer program code or software 56 (FIG. 6) may further comprise a third module 63 adapted to receive stored data of a record file 80 from the second module 62, to apply such stored data to a predictive model to generate predictive data values over a desired period for such record file as a predictive outcome, and to transmit such predictive outcome to a desired storage. In another option, control computer program code or software 56 may comprise a third module 63 adapted to receive stored data of a record file 80 from the second module 62, to apply such stored data to calculate changes in the amplified signal data over a desired period, and to transmit such changes to a desired storage. In yet another option, control computer program code or software 56 may comprise a third module 63 that is adapted to receive stored data of a record file 80 from the second module 62, to apply such stored data to calculate changes in the amplified signal data from background radiation data over a desired period, and to transmit such changes to a desired storage.

In one embodiment, the signal data comprises a plurality of pulses at a pulse frequency over time, and wherein the first module 61 is adapted to communicate a sampling frequency instruction to the sensor processor 22, the sampling frequency instruction being a function of the pulse frequency of the signal data. The first module 61 may be adapted to communicate an increasing sampling frequency instruction upon an increase in pulse frequency.

Processes that could be used in the manufacture of the measurement sensors 11 or other components may include many that are common within the electronics assembly industry, along with the following specific processes. For an embodiment of the system 10 that includes a gamma radiation mask or shield 38, for example, this mask or shield 38 may be glued, molded, swaged, screwed or otherwise mechanically fixed into the measurement sensor housing 25. Then, the mask or shield 38 may be used as a mounting plate for the other measurement sensor 11 components, including electrical components and additional housing components to create a lightproof sensor housing 25.

In another embodiment, the measurement sensor 11 components may be arranged within the measurement sensor housing 25, and then an epoxy, silicone or other curable fluid could be applied surrounding the components. This method would hold the optical components in alignment while also surrounding them with a light proof material.

In another embodiment of the measurement sensor 11 that includes a wireless output port 27 as an antenna, it may be embedded in the structure of the measurement sensor housing 25. For example, antenna wire may be arranged on a mold form, then molding plastic may be applied around the form thus encapsulating the wires. With this method, the antenna wires could be of numerous designs for the optimization of antenna efficiency. Additionally, this method could allow for a ferrite material to be placed within the antenna portion of the housing 25 to further optimize the antenna efficiency.

Figure 11:
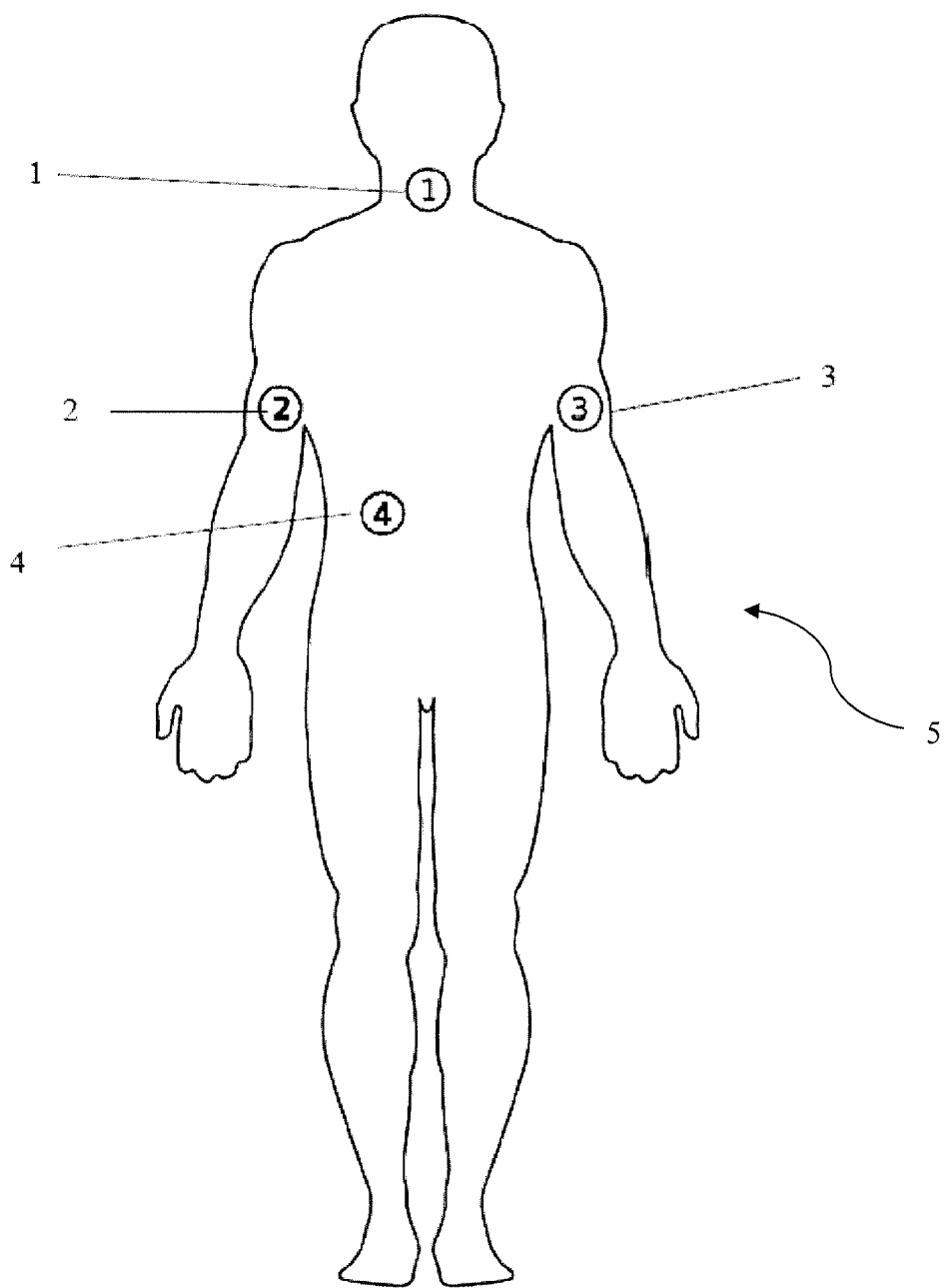
FIG. 11 is a diagram illustrating locations on a subject's body where sensors may be placed.
Figure 12:
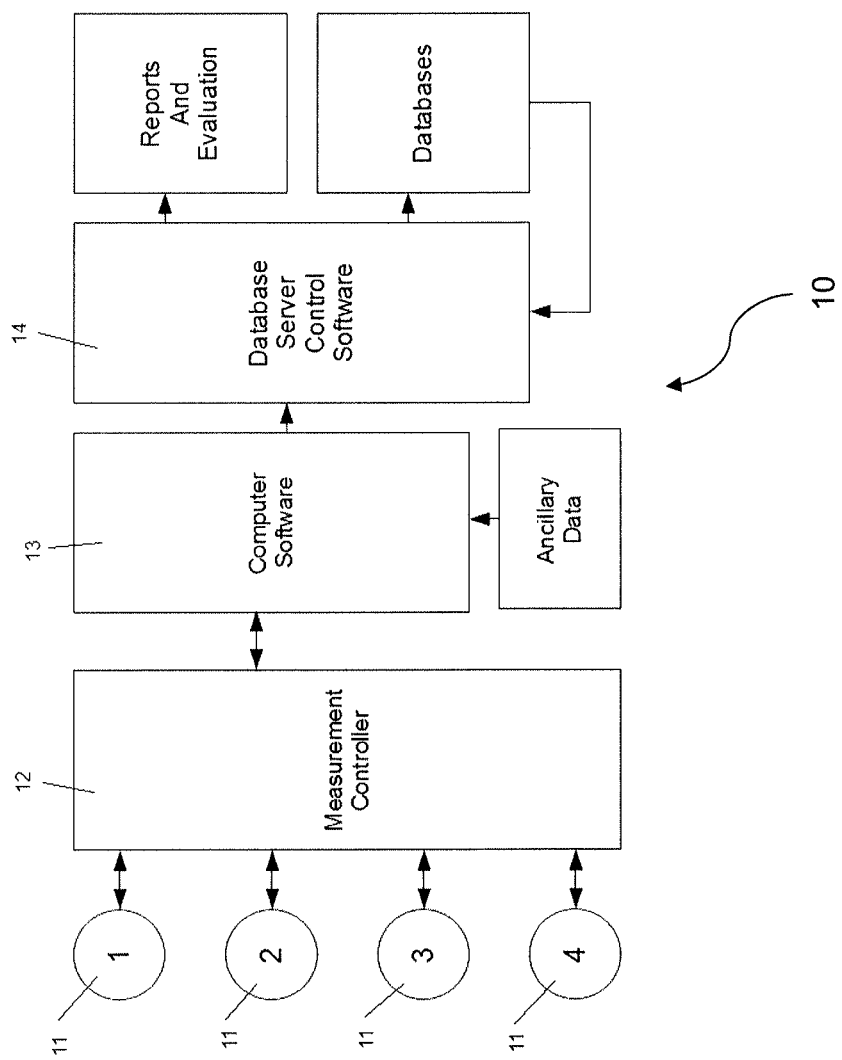
FIG. 12 is a flow diagram of an embodiment of components the system.
Figure 13:
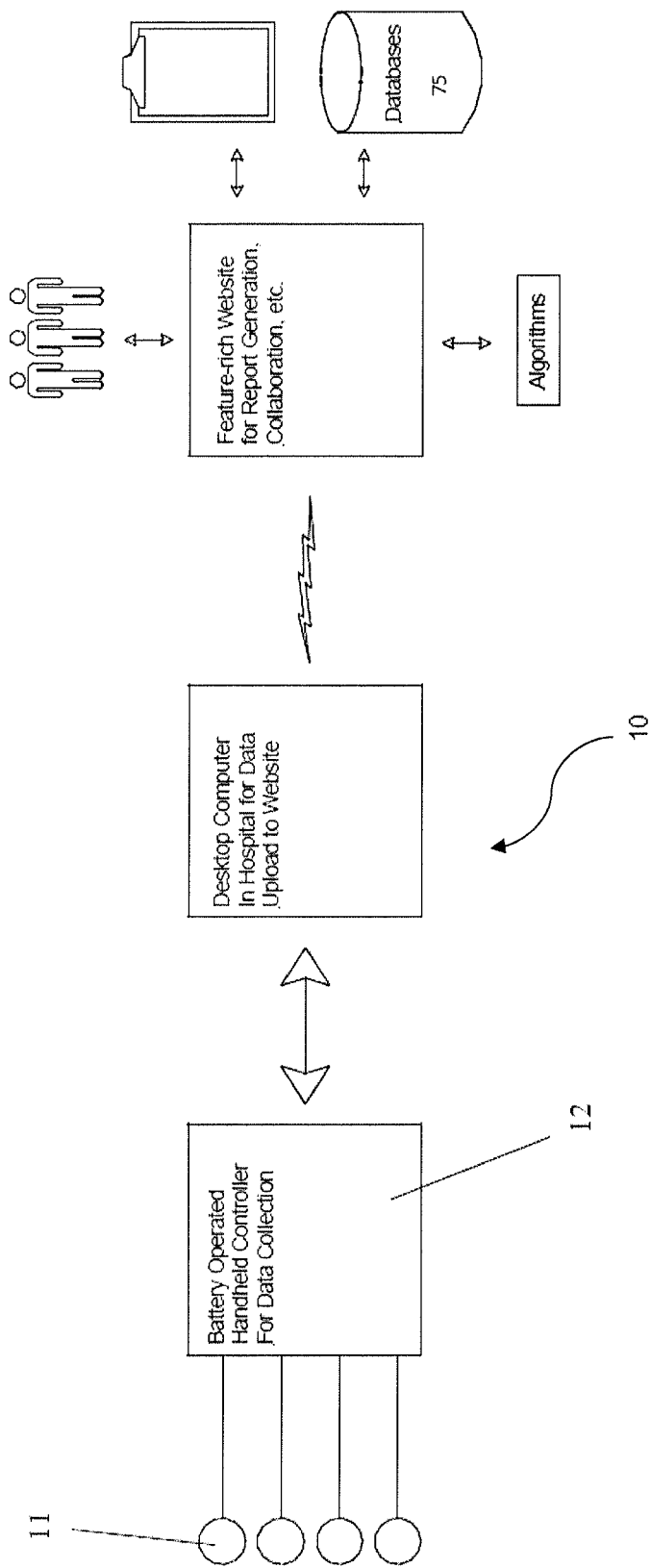
FIG. 13 is a schematic diagram illustrating aspects of an embodiment of the system.

Additional aspects or optional embodiments are provided below. The present system enables (but does not require) radiation sensitive sensors to be placed ex vivo, such as on a test subject's skin. These sensors may measure the localized uptake of a radio-labeled tracer which is injected into the subject 5. In an embodiment as shown in FIG. 1, measurement sensors 11 may be placed in one or more of the following locations of FIG. 11, for example: (a) directly over the tumor 1; (b) on the upper right arm 2, approximately 10 cm above the antecubital fossa; (c) on the upper left arm 3, approximately 10 cm above the antecubital fossa, and (d) over the liver 4, immediately below the ribs and directly below the nipple. As shown in FIG. 2, for example, an embodiment of the system 10 may comprise: (i) one or more measurement sensors 11; (ii) a measurement control device 12; (iii) computer software or computer program code 13 capable of executing certain functions, such as measurement and generation of predictive data. The system 10 may also include a desired storage for data, etc., with appropriate databases, database management or server control software 14, etc.

Figure 14:
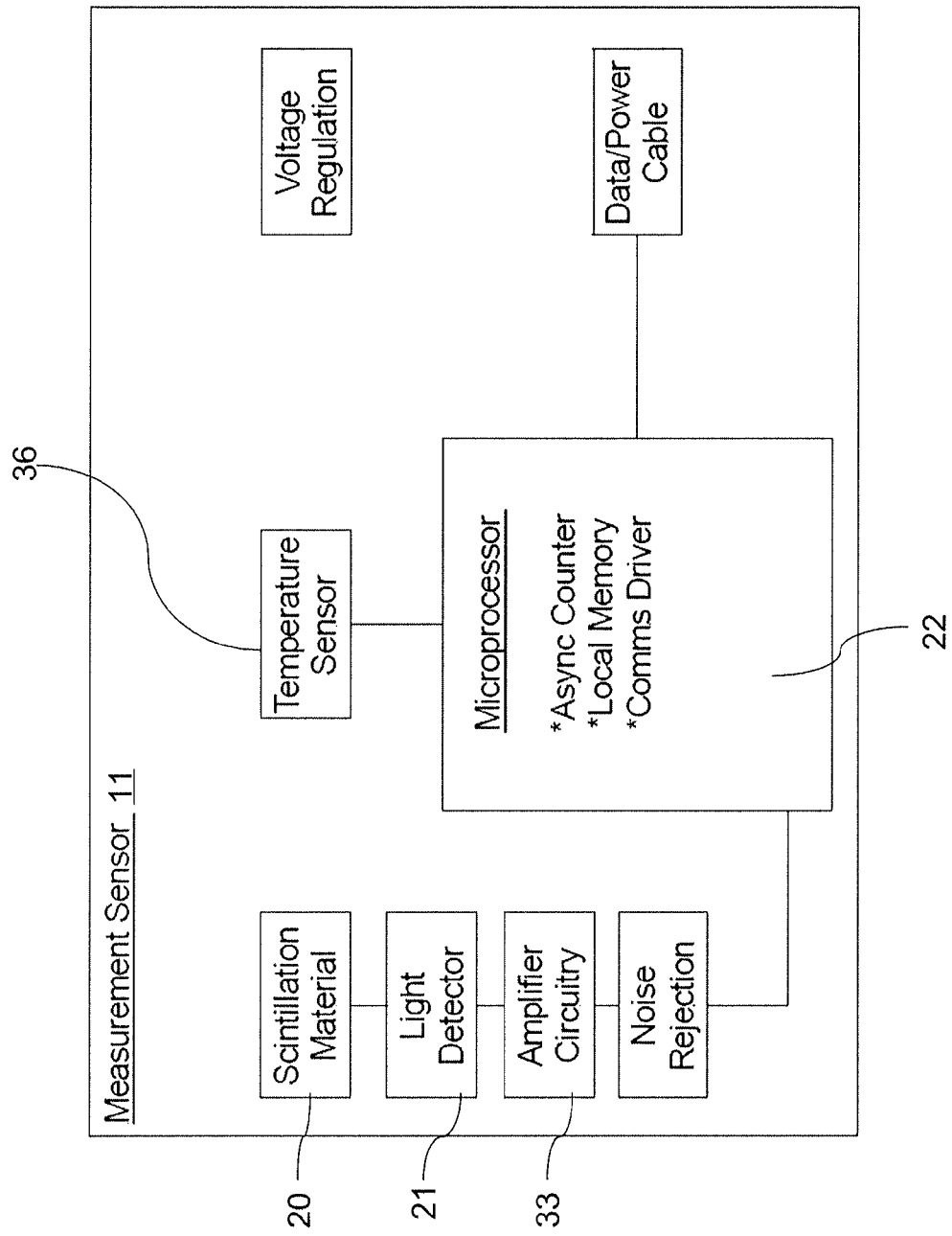
FIG. 14 is a schematic of an embodiment of a measurement sensor.
Figure 15:
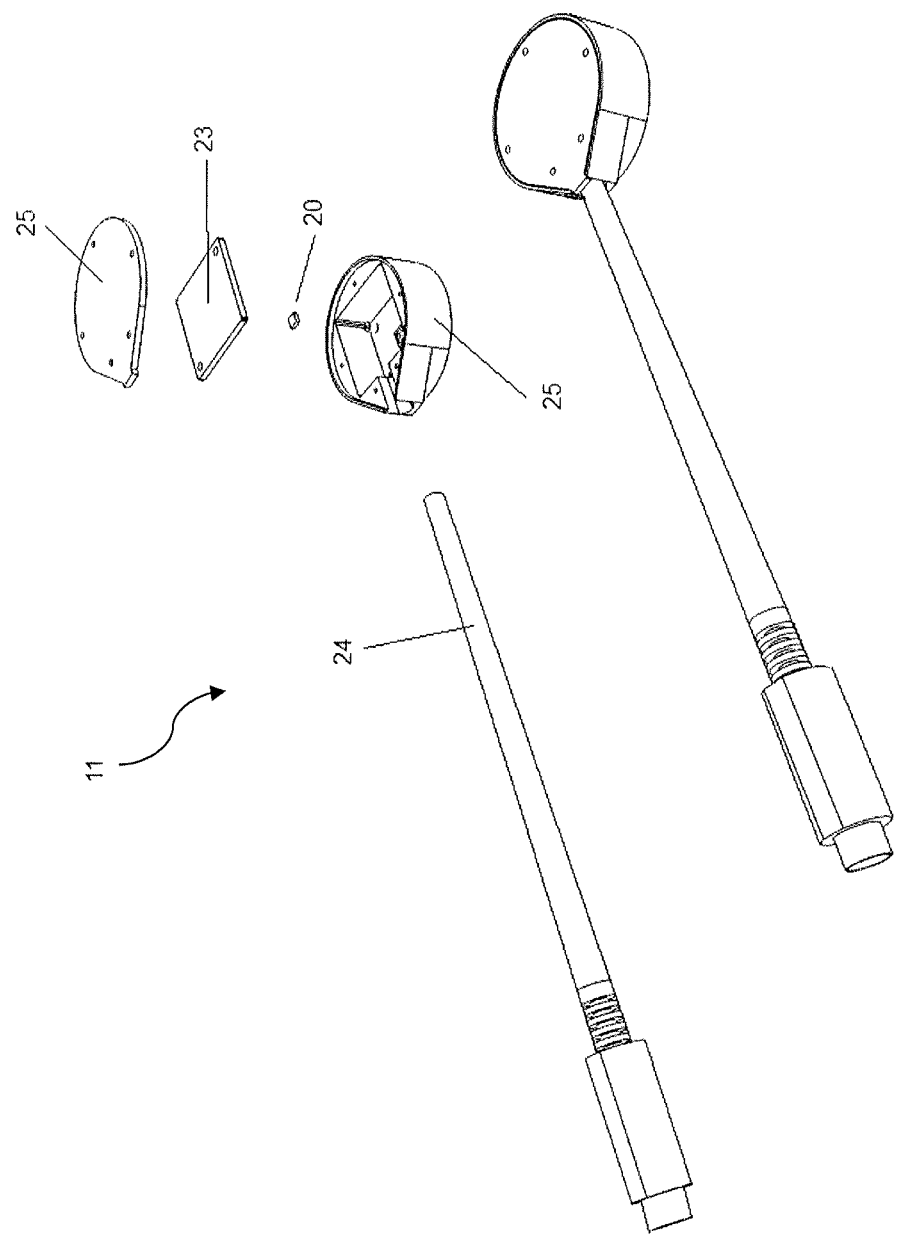
FIG. 15 is a schematic diagram illustrating aspects of an embodiment of a measurement sensor.
Figure 16:
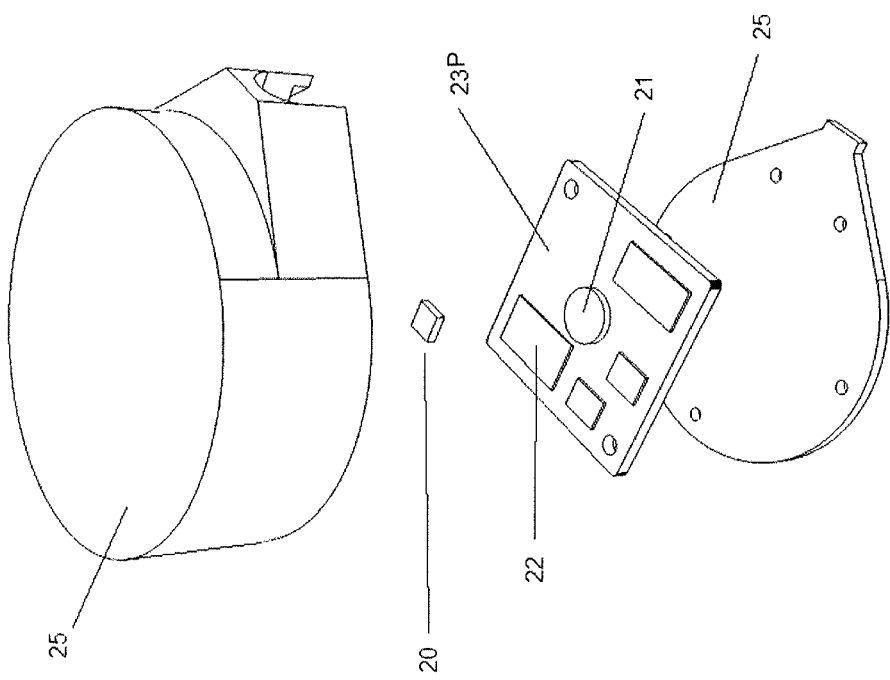
FIG. 16 is a detailed exploded view of an embodiment of a measurement sensor.
Figure 17:
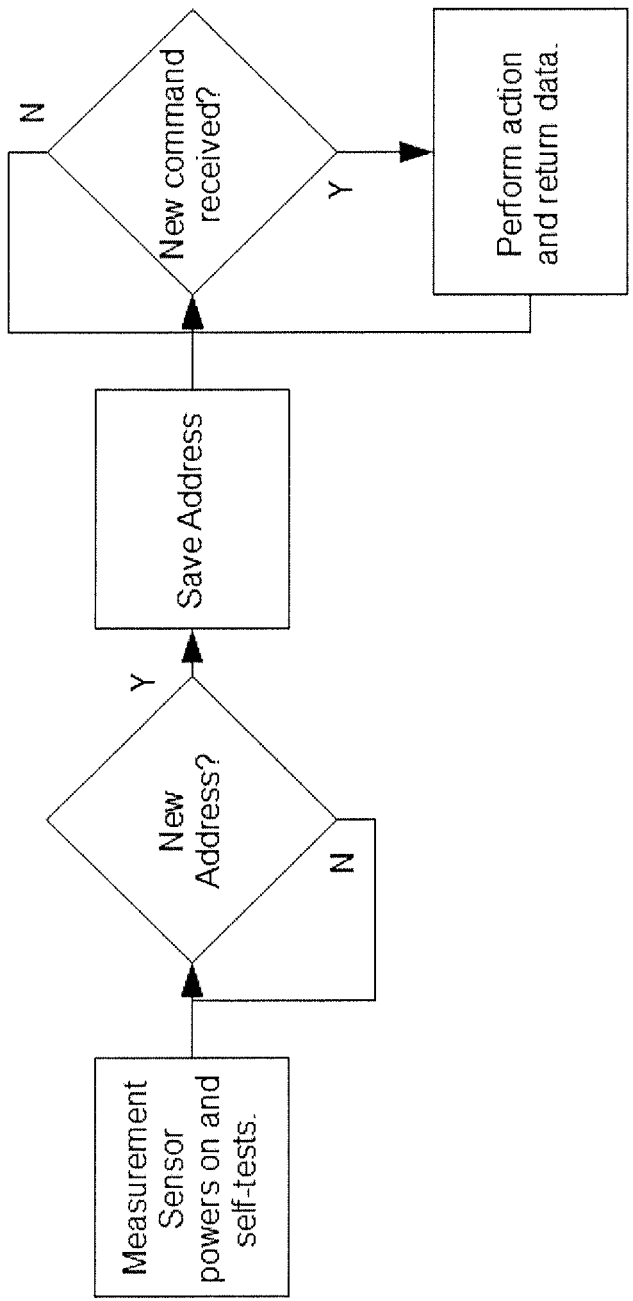
FIG. 17 is a flow diagram illustrating an embodiment of measurement sensor operation.
Figure 18:
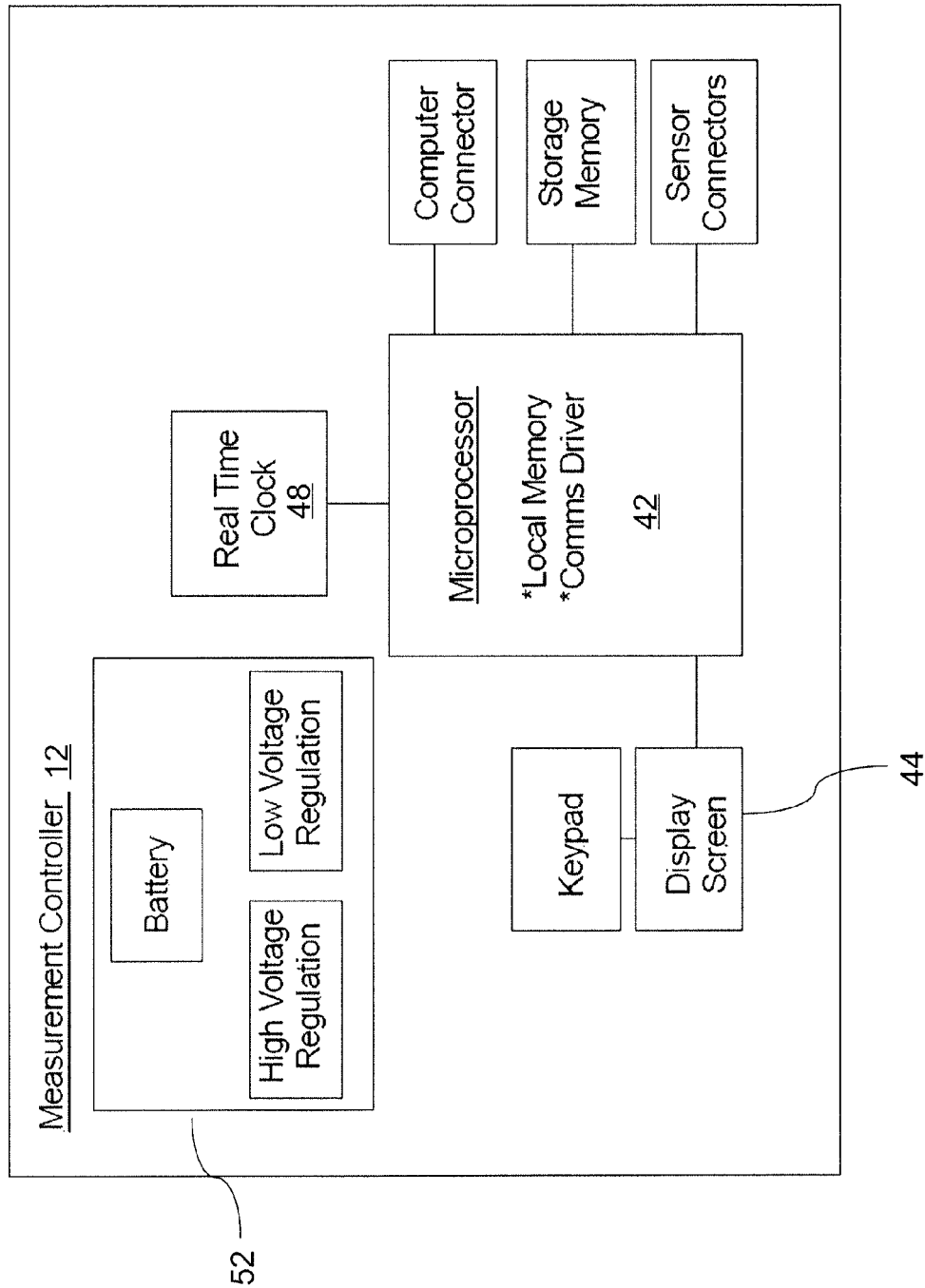
FIG. 18 a schematic diagram illustrating aspects of an embodiment of a measurement control device.
Figure 19:
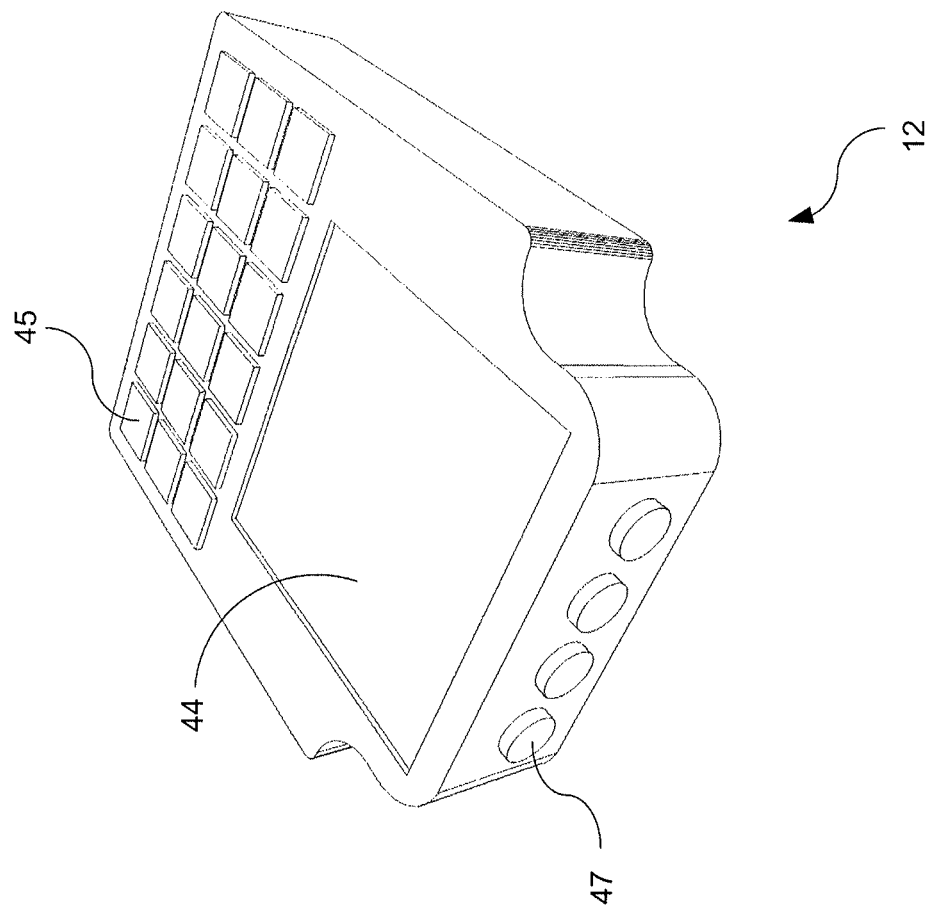
FIG. 19 is a front prospective view of an embodiment of a measurement control device.

As shown in FIGS. 14 through 16, a measurement sensor 11 can be, for example, a device comprising a scintillation material 20; a light detector 21; and a sensor processor 22 with associated non-transient sensor memory 30, logic or sensor software 26, and other circuitry supporting these components in operable communication, optionally with a printed circuit board 23P (FIG. 16). FIG. 17, for example, illustrates a flow diagram of operation of an embodiment of an ex vivo measurement sensor 11. In operation, a subject 5 may receive a systemic administration by injection of a radioactive substance (also referred to as a tracer). When this radioactive substance decays, it releases or emits positrons (also referred to as high energy particles). The measurement sensor 11 uses a scintillation material 20 to receive gamma radiation from positron emission decay and to convert the radiation into photons, such as pulses of light, which may then be detected by the light detector 21. The sensor processor 22 may enable measurement and collection of the photons, such as the number of light pulses detected over a given amount of time. For example, a large number of light pulses detected per unit of time may correspond to a large concentration of radioactive material. As the radioactive material concentration changes, the light pulses detected per unit of time changes accordingly. By graphing the light pulses counted versus time of data collection, a visual representation of radioactive concentration over time may be produced. This graph indicates how the radioactive concentration is changing.

Any number of small embedded processors are adequate for use in the measurement sensor 11, and sensor processor 22 may include a dedicated asynchronous counter of suitable size, if need for the application and if an external one is not included in the additional circuitry. The sensor processor 22 may be embedded in the measurement sensor, or an external sensor processor 22 may be provided as applicable. The sensor processor 22 may be specially configured to satisfy various embodiments of the system 10, depending on the requirements of the application. An FPGA or other programmable logic device, for example, may be well suited to this system, possibly incorporating a microprocessor sub-system within the FPGA design.

Possible scintillation materials 20 include, but are not limited to: Bismuth Germanate (BGO); Gadolinium Oxyorthosilicate (GSO); Cerium-doped Lutetium Oxyorthosilicate (LSO); Cerium-doped Lutetium Yttrium Orthosilicate (LYSO); Thallium-doped Sodium Iodide (NaI(Tl)); Plastic Scintillator (Polyvinyltoluene); or Cadmium Zinc Telluride (CZT). In an embodiment of a measurement sensor 11, multiple scintillation materials 20 adapted to measure different radioisotopes may be used. In another embodiment of a measurement sensor 11, scintillation materials 20 that do not require the use of a light detector 21 may be used. In another embodiment of a measurement sensor, multiple scintillation materials 20, each with their own detection circuitry, may be included to enable a two dimensional array of measurements.

In an embodiment of measurement sensor 11, the light detector 21 may include a signal amplifier 33 or amplification circuitry to handle low level signals. In another embodiment, measurement sensor may further include a temperature sensor 36 which is coupled to a temperature compensator 50, the temperature sensor adapted to measure an ambient or local temperature of the scintillation material 20 and light detector 21, and to communicate or report such temperature to temperature compensator 50. Temperature compensator 50 being adapted to generate a temperature correction factor based on comparison of the ambient temperature to a reference temperature. The temperature compensator 50 may apply the correction factor to the signal data to produce temperature compensated signal data, or may be adapted to reporting the local temperatures of the scintillation material 20 and light detector 21. Depending on the embodiment, in vivo detection may not require temperature compensation in that the measurement sensor 11 might be calibrated for normative subject temperatures.

In another embodiment of the system, a measurement sensor 11 can be, for example, a device comprising a scintillation material 20; a light detector 21 and associated signal amplifier 33 or amplification circuitry and sensor processor 22 located on a printed circuit board 23P in the sensor portion of the system. Light detector 21 may be selected based on the application, such as a photodiode or photocathode, and signal amplifier 33 (or amplification circuitry, possibly incorporated into circuit board 23P) may include a photomultiplier or simply a signal amplifier 33. Other associated circuitry may then moved to the measurement control device 12. In any number of embodiments, the measurement sensor 11 can be provided with microelectromechanical machine (MEMS) power generation capability such that a battery or external power source is not necessary. A MEMs generator may be piezoelectric based, adapted to generate electricity from a motion of the subject 5, body heat of the subject 5, or the blood pressure of subject 5. Alternatively, sensor power supply 32 may be a corded power connection to either the control device. In another embodiment, a measurement sensor 11 can be a wireless, with an independent power supply 32.

In an embodiment of a measurement sensor 11, for example, the electronics may be enclosed in a light-proof enclosure or housing 25 and there can be a multi-conductor cable 24 for data communications. Mechanical design of the housing 25 can be used to accurately control the placement of the scintillation material 20.

In an embodiment of a measurement sensor 11, the sensor may include sensor housing 25 which optionally may incorporate a shielding mask 38 for collimation of the incoming radiation for increased directional sensitivity. The shielding mask 38 can be made of any number of dense materials including, but not limited to: lead, steel, iron, aluminum, iridium, platinum, copper, cement, dense plastic, etc. The shielding mask 38 can be tailored to protect against specific radiation depending on the application of the system of the present invention.

In an embodiment of a measurement sensor 11, for example, the sensor could further include a removable and/or disposable protective sleeve or case, also referred to as carrier 35. This sleeve or carrier 35 can have adhesive (e.g., adhesive 35A) applied in order to attach the measurement sensor 11 to a test subject 5. This sleeve can also be used as a sanitary barrier between the measurement sensor 11 and a test subject 5. In some embodiments, measurement sensor 11 may further include housing 25 which itself has adhesive used to attach the sensor 11 to a test subject 5.

In any number of embodiments, measurement sensor 11 and measurement control device 12 may include the necessary hardware and software to enable wireless communications between them. In such an embodiment, encryption techniques may be used to provide security for wireless signals.

In any number of embodiments of the system of the present invention, an individual measurement sensor can be calibrated for radiation sensitivity. This calibration can overcome measurement inconsistencies due to manufacturing and physical tolerances in the sensor. Since each measurement sensor 11 has unique manufacturing and physical tolerances and material characteristics, no two sensors will naturally report the same measurement given the same radiation source input. Therefore, each sensor may be exposed to a known activity radiation source and a correction factor can then be provided for each individual sensor. As a result, each measurement sensor 11 used in the system 10 may be calibrated with one another with regard to radiation sensitivity.

In any number of embodiments, an individual measurement sensor 11 may be calibrated for temperature sensitivity. Various components of a measurement sensor 11 are sensitive to temperature changes and the reported radiation activity due to temperature. It is known that a scintillation crystal or material 20, a light detector 21, and, to a lesser degree, amplifiers used for light detection, for example, may be sensitive to temperature. Therefore, a precision temperature sensor 36 may be placed locally or proximally to the temperature sensitive elements. Ambient temperature can then be recorded during the data collection process so that corrections or compensation can be made to signal data or measurement readings in order to compensate for any inaccuracies in the measurement readings resulting from certain elements' sensitivity to temperature, producing temperature compensated signal data. In order to determine temperature correction factors, a measurement sensor 11 may be subjected to a stable radiation test source while the surrounding temperature is swept through the range of the operating temperatures. This may be accomplished in a laboratory temperature chamber. Through this test process, radiation activity of a known, stable source as well as temperature data can be recorded. A calibration curve can then be calculated which adjusts the measured radiation activity to a normalized flat response corresponding to expected compensated signal data.

In another embodiment, a measurement sensor 11 may provide adaptive performance and measurement capabilities. For example, if the rate of tumor growth accelerates, the sensor can automatically respond to the change by increasing sampling frequency.

In any number of embodiments of the system, a measurement control device 12 can be, for example, a hand-held and battery powered device comprising a display screen, a keypad and data communications connectors. In an alternative embodiment of the system of the present invention, the measurement control device 12 can be a desktop-style powered device. In another embodiment, the measurement control device 12 or other portions of system 10 may include a cradle-style charging dock for the battery operated device. The cradle-style charging dock can charge batteries for a hand-held device and can also initiate the capture of any measurements in the hand-held device's memory. In another embodiment, the measurement control device 12 may provide MEMS power generation capability such that a battery or external power source is not necessary.

Figure 20:
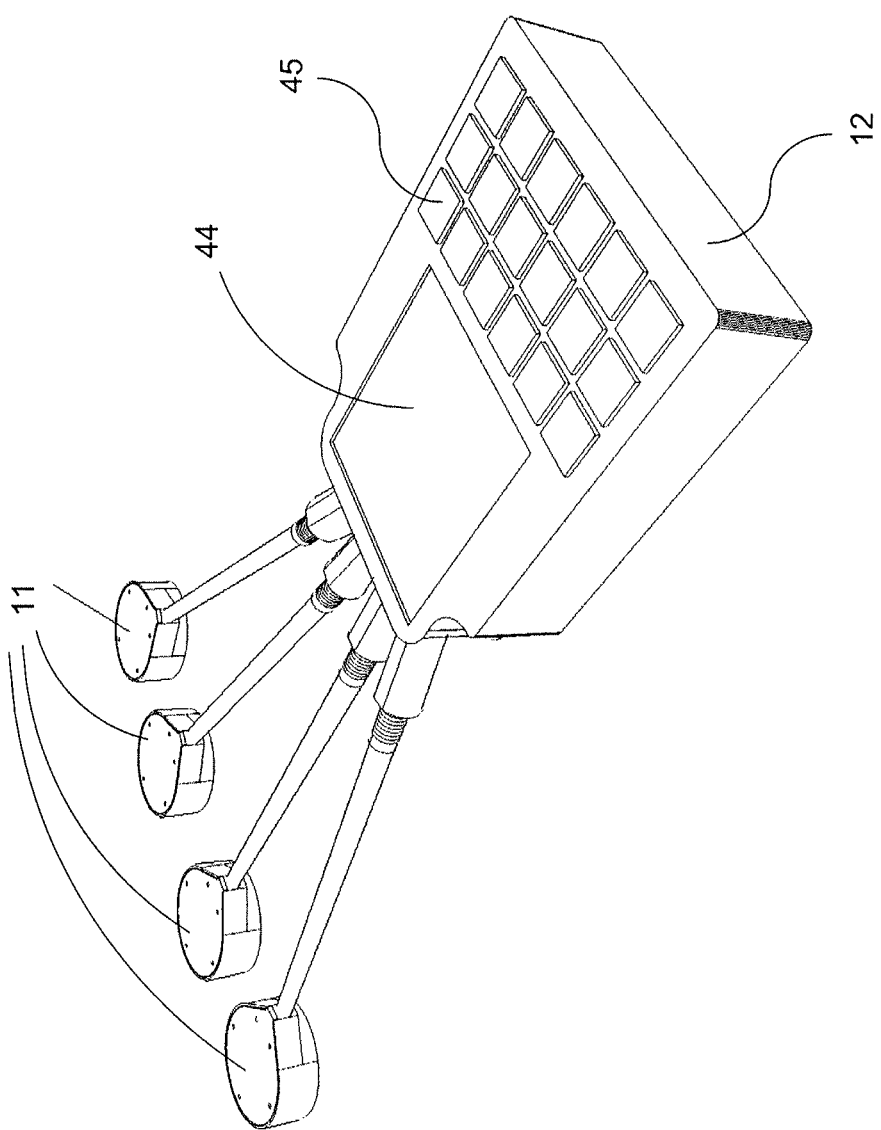
FIG. 20 is a front prospective view of an embodiment of a measurement control device with measurement sensors attached.
Figure 21:
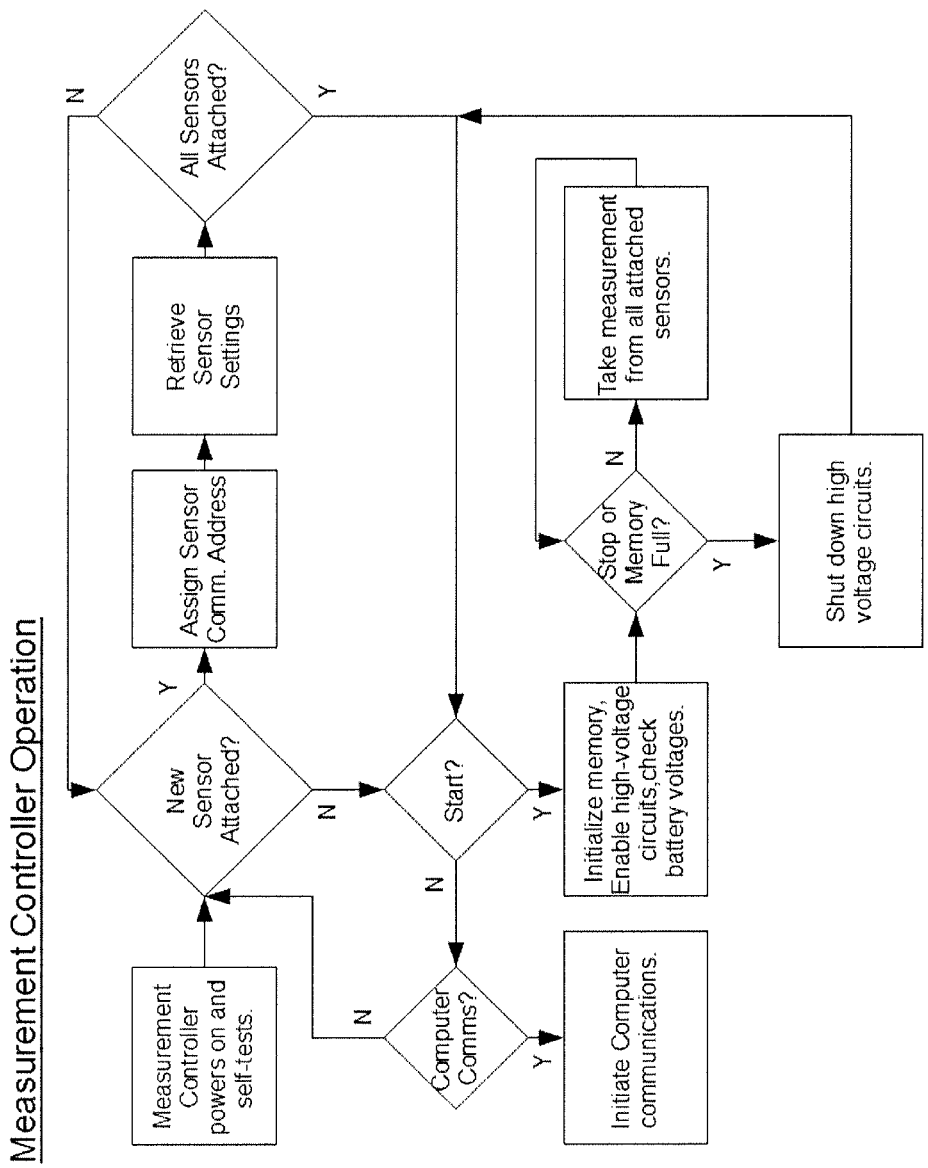
FIG. 21 is a flow diagram illustrating measurement control device operation in an embodiment.
Figure 22:
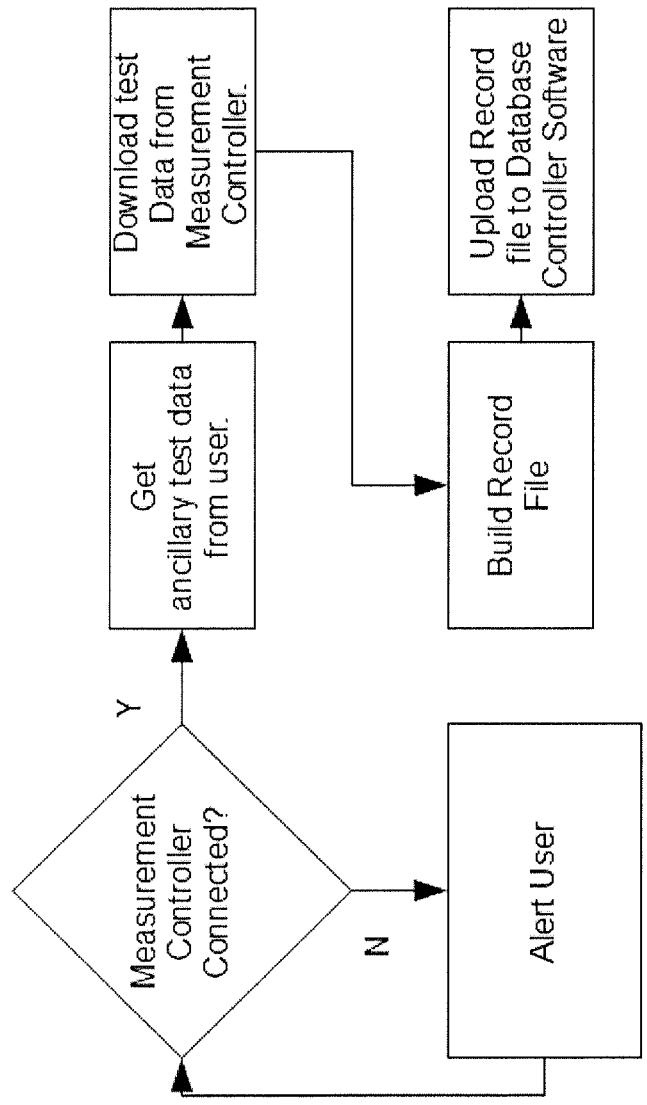
FIG. 22 is a flow diagram illustrating computer software operation in an embodiment.
Figure 23:
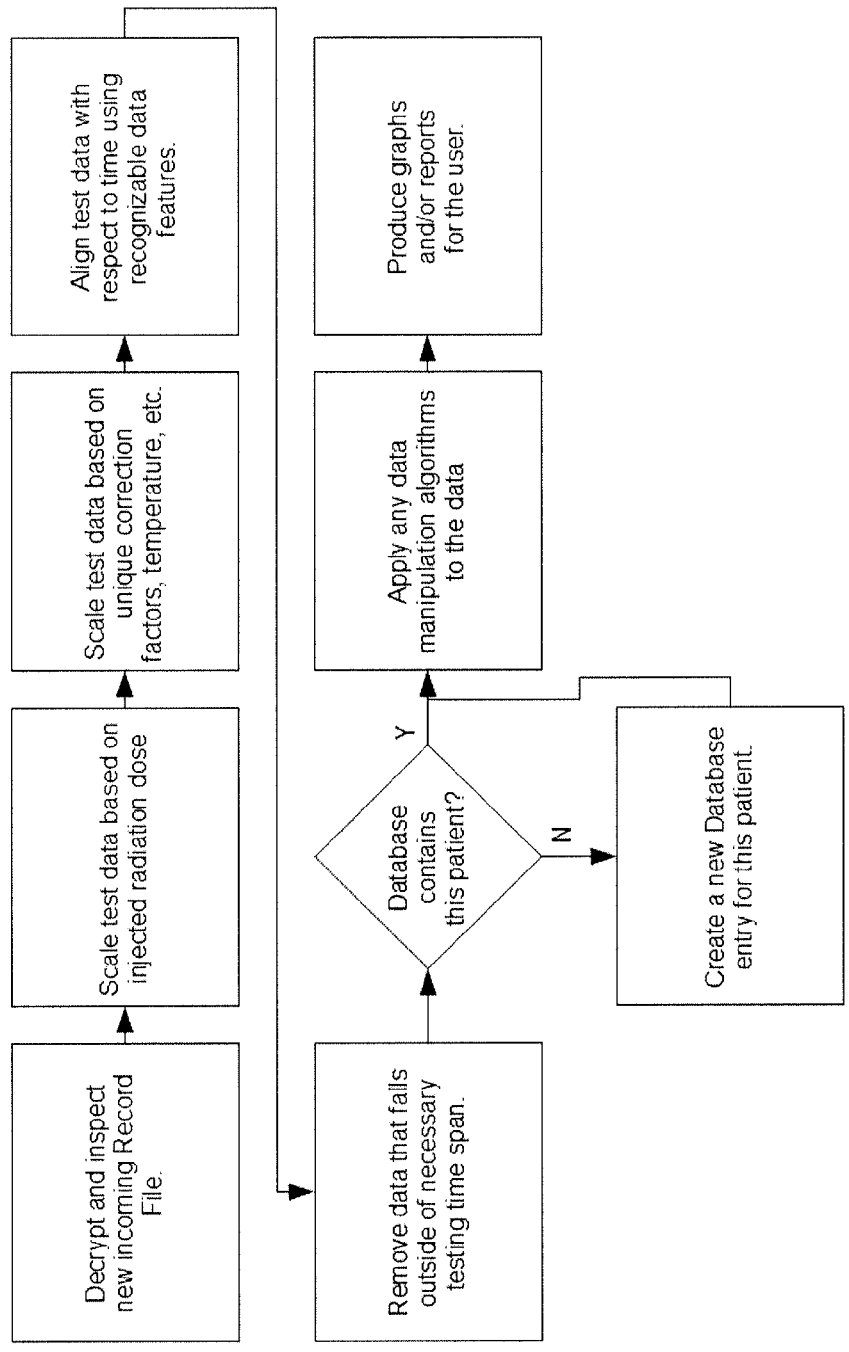
FIG. 23 is a flow diagram illustrating database controller software operation in an embodiment of the system.

In any number of embodiments of the system 10, as shown in FIGS. 20 through 21 for example, a measurement control device 12 comprises a control processor 42, control software 56 (optionally as embedded software), control memory 40, a real-time clock 48, and other associated logic and circuitry on a printed circuit board. The control processor 42 may be embedded in the measurement control device 12, provided as an external processor, or optionally merged with station 70. The control processor 42 is generally specially configured to satisfy embodiments of the system 10. The control device can control user-interface, data collection, and data transmission activities. There are various microprocessors capable of this including small embedded processors and single-board computers. FIG. 21 is a flow diagram illustrating operation of an embodiment of a measurement control device 12. The system 10 generally may respond to user input, keep track of sensor attachment or association, monitor operational parameters, such as battery level, and transfer measurement data to a desired storage, such as an external computer. In an embodiment of a measurement control device 12, as illustrated in FIG. 20 for example, there can be multiple data communications connectors to enable the attachment of multiple measurement sensors 11, as well as a data communication to a variety of desired storage devices or networks.

In an embodiment of a measurement control device 12, the device can further include network connectivity and control hardware and software to incorporate the functionality of the control computer software 56. This creates a stand-alone system at the test site which eliminates the need for a separate computer or computer software. Encryption and decryption methods known in the art can be provided in any number of embodiments to secure wireless communications.

An embodiment of a measurement control device 12 may further include a bar code scanner for recording pertinent identification numbers, calibration codes, etc. when printed on bar codes. An embodiment of a measurement control device 12 can further include a pulse-oxygen, skin resistivity, or other biological sensor in order to incorporate additional data into the measurements collected. Another embodiment of a measurement control device 12 can further include a digital camera system for incorporating photos into the data record file. These photos could be used for sensor placement details, for example. One embodiment of a measurement control device 12 can further include functionality which communicates to the user specific details pertinent to the test or test subject being worked with. This communication can include, but is not limited to, non-standard placement locations for the measurement sensors 11, reminders of tumor size and location, general notes, test related photos, etc.

In an embodiment of a measurement control device 12, for example, a power switch can control power to all components of the device, except possibly a real-time clock 48. The clock 48 may have consistent back-up power to avoid losing the programmed date and time. When the power switch is in the "ON" configuration, power may be applied to the device components, and a microprocessor can start operation and test operability. The microprocessor of control processor 42 may further test external peripherals such as the display 44, the real-time clock 48, etc. As the tests are performed, a display screen of the measurement control device 12 may display, for example, a waiting message. Next, at least one measurement sensor 11 may be attached to the control device 12 via a connector and a cable, such as multiconductor cable 24. Upon attachment of a measurement sensor 11, the control device 12 recognizes the attachment and performs duties described below to start up the measurement sensor 11.

In an embodiment of a measurement sensor 11, for example, power may be supplied to the sensor via the measurement control device 12. For example, a multi-conductor cable 24 with a connector on the end or a plug that fits into a mating jack can be used to connect the measurement sensor 11 to the control device 12. Power can be supplied to the measurement sensors 11 over this cable from the measurement control device 12. The sensors can be connected to the measurement control device 12 before data collection and remain connected throughout data collection. In another embodiment, the measurement sensor 11 may include its own sensor power source 32 and non-transient sensor memory 30 to store recorded data such that no cable might be necessary and the sensor does not need to remain connected to the measurement control device 12 during operation. In order to retrieve the recorded data, wireless communications may be enabled and/or a cable may be connected to the measurement control device 12 at a desired time.

After power is turned on to the sensor 11, as shown in FIGS. 17 and 21 for example, the sensor processor 22 may start operation and test itself. If the self-test verifies that the measurement sensor 11 is operational, the sensor can alert the measurement control device 12 that the measurement sensor 11 is operational and ready to receive an address which is an address that the control device 12 will use to communicate with the identified measurement sensor 11. The measurement control device 12 can next send the measurement sensor 11 a unique address or identifier 16 assignment (i.e., unique being sufficiently individualized for the application to avoid confusion). After receiving the unique identifier 16 assignment, the measurement sensor 11 can accept the unique address and listen to a communications bus for commands specific to the individual sensor. A measurement control device 12 may send any of the following commands to any of its connected sensors: (1) connection check using the sensor's unique address; (2) Sensor LED on/off; (3) Set sensor PWM output; (4) Read/Write sensor EEPROM; (5) Measure Temperatures; and/or (6) Measure Radiation pulses for a set time period (for example, one second). Other commands not specifically listed can be sent by the measurement control device 12. After the measurement control device 12 sends a command to the measurement sensor 11, the sensor performs the commanded action and replies with a result if necessary.

In any number of embodiments of the system, when one or more measurement sensors 11 are attached to a measurement control device 12 and the sensors are operational, the measurement control device 12 can indicate, through a message on the display screen, for example, that the device is ready to begin data collection. When a user begins data collection, the measurement control device 12 first downloads each sensor's individual calibration data and stores the calibration data into control memory 40 or other desired memory or storage. The control device 12 can then request for a measurement of temperature and radiation pulses, for example, from each attached measurement sensor 11. All received readings can be stored, along with a time stamp, in the control memory 40. When the control memory 40 might be full or if the user stops the data collection, the measurement control device 12 may simply stop accepting readings from the measurement sensors 11. A user may download the saved data collected from the control memory 40 to a computer or other desired storage.

In any number of embodiments, computer program code used in the system may be capable of: (1) performing diagnostic tests on the measurement control device 12; (2) transferring measurement data from the measurement control device and saving it to a record file; (3) gathering ancillary test data from the user or other sources (radiation dose administered, test subject weight, PET scan data, etc.) and including it in the data record file; and (4) transferring the data record file to the database server control software. In any number of embodiments, database server control software can accept incoming data record files from the computer software and apply one or more algorithms to the data received. Measurement data may be stored in an optional central database 75 while the algorithm output can be used to generate reports for the user. These reports can indicate estimated parameters or even estimated future parameters of a tumor.

In an embodiment of the system, for example, a user may attach a measurement control device 12 to a computer and run computer software to transfer measurement data stored on the measurement control device 12 to the computer. The computer software or program code communicates with the control device 12 to determine what type and how much data is available for downloading. The computer software can ask the user for pertinent test-related information such as radiation dose administered, identification or number of test subject 5, placement locations of the sensors, tumor location and type, etc. Once measurement data has been transferred from the measurement control device 12 to the computer, a data record file can be built. Once complete, the data record file can be transferred to a database server and predictive model or algorithm system.

In any number of embodiments, pre-processing operations may be performed on a test subject data set. Session measurements for all channels can be normalized with respect to injected radiation dose, for example. The dose is recorded during the test and is used to adjust measurements on a scalar basis. A session is one specific data recording event which includes sensor placement on the subject 5, injection of radioactive material, and collection, recordation and transfer of recorded data. Measurements from each session can be aligned so that the rising edge on a "trigger" channel—right or left arm—is at time zero. The term "trigger" channel is used to mean a sensor that is sure to see a large amount of radioactive material so that it is ensured to have a dramatic and easily recognizable increase in the measurement. Having a rapidly changing "step" like this allows for time-alignment of data sets recorded at different times or "sessions." Any data which is before a predetermined time or after the predetermined time (for example, data before time −120 seconds or after time 3600 seconds) can be removed from the measurement data. In addition, session measurements for all channels can be normalized with respect to temperature sensitivity. Individual sensor's temperature correction coefficients can be retrieved and used to correct the radiation pulse count measurements.

In any number of embodiments of the system, session measurements for all channels can also be adjusted to account for the natural decay of the radioisotope used, for example. The radioisotope naturally decays in the test subject and this adds a decreasing function to the measurement data. Accounting for this natural decay and removing any data attributed to the natural decay can portray the data as the amount of radiation encountered without the decay function included.

In any number of embodiments of the system 10, measurements may be aligned with respect to the control channel(s). Control channels are stable and repetitive, therefore aligning all channels will make differences in the non-control channels visible.

In one embodiment of the system 10, a database server and predictive model may be provided. A hardware server which runs software to incorporate incoming data record files from the computer software and to save this incoming data to a database file along with data previously saved; and database server control software. FIGS. 14 and 15, for example, illustrate flow diagrams of operation of an embodiment of the computer software and the database server control software respectively. The database server and predictive algorithm system or model can apply one or more algorithms to this saved database in order to estimate parameters specific to the tumor under test or a group of tumors. Additionally, the database server control software can apply one or more models or algorithms in order to predict future parameters of the tumor or a group of tumors. The database server control software can also use the output of the algorithms to generate report files for the user which present the estimated and/or predicted parameters.

In an alternative embodiment of the system 10, a database server and predictive model comprises a dynamic website with server software running behind it, which allows for a multiple-user system for analysis and reporting. In another embodiment, the database server and predictive model or algorithm system further includes functionality which transfers the algorithm output and report back to the computer software for analysis and interpretation by the user. In one embodiment, the database server and predictive model further includes functionality which can provide real-time communication and updates about sensor data; notification parameters (e.g., situations with tumor development); and/or alert conditions.

In an alternative embodiment of the system 10, database server control software keeps a database of all measurement data that has been submitted previously. Any new data record files that are submitted can be added to the database. The user can include other data records such as, but not limited to, results from other tests (PET Scan, CT Scan, etc.), information about a particular subject (height, weight, etc.), or general notes, for example. The user can use the database server control software to generate graphs of measured data, to calculate various functions of the measured data and then graph those functions if necessary; and/or to apply prediction algorithms to the data. The prediction model may be capable of, although not limited to: (1) predicting the future outcome of tumor treatments; (2) predicting which tumor treatments have the best chance of success; (3) predicting the likelihood that metastatic disease is present in the subject; and/or (4) other. The database server control software can generate reports for the user of measured data and/or predictions based on the data. These reports include, but are not limited to, graphs, predictions with confidence levels, etc.

In any number of embodiments of the system of the present invention, the class of algorithms used is of the classification structure in machine learning. These algorithms use a training set of data to build a model of the data. Then, when new unknown data sets are introduced, the algorithms can determine where in the model the new data should fit. This approach allows for the system of the present invention to inspect a submitted data set and determine whether and how closely it has seen examples like the submitted data set in the past. If there have been similar examples in the past, the system can predict the outcome of the current data set based on the outcomes of the past data. For example, if there are various past examples that closely match the new data submitted, the algorithm can determine which treatments in the past led to the most favorable outcome. Physicians may then select treatments with the best outcome. In another embodiment, the algorithms can provide adaptive performance and measurement capabilities. For example, if the rate of tumor growth accelerates, the system can automatically respond to the change by increasing sampling frequency.

In an embodiment of the system 10, the ways in which new data submitted is matched to previously seen data or determined not to match any of the previous data are based on multiple mathematical or quantitative functions that can be applied to measurement data. For example, area under the curve, polynomial curve fit to a portion or all of the data, the ratio of two data measurement channels, etc., are all ways in which data sets can be matched.

It will be apparent to one skilled in the art that a computer system that includes suitable programming means or modules for operating in accordance with the disclosed methods also falls well within the scope of the present invention. A specially configured computer system including suitable programming means to satisfy the objects described above can be provided. Suitable programming means include any means for directing a computer system to execute the steps of the system and method of the invention, including for example, systems comprised of processing units and arithmetic-logic circuits coupled to computer memory, which systems have the capability of storing in computer memory, which computer memory includes electronic circuits configured to store data and program instructions, with programmed steps of the method of the invention for execution by a processing unit. Aspects of the present invention may be embodied in a computer program product, such as a non-transient recording medium, for use with any suitable data processing system. The present system can further run on a variety of platforms, including any of a variety of software operating systems. Appropriate hardware, software and programming for carrying out computer instructions between the different elements and components of the present invention are provided.

The invention may be embodied in other specific forms without departing from the spirit or essential characteristics thereof. The present embodiments are therefore to be considered in all respects as illustrative and not restrictive, the scope of the invention being indicated by the claims of the application rather than by the foregoing description, and all changes which come within the meaning and range of equivalency of the claims are therefore intended to be embraced therein.

What is claimed is:

1. A system for the ex vivo real-time detection of gamma radiation emitted by a subject from systemic administration and uptake of a radioactive analyte that decays in vivo over a period of time by positron emission, the system comprising:
at least one ex vivo measurement sensor having a sensor housing, a scintillation material, a light detector, a temperature sensor, a signal amplifier, a sensor processor, a non-transient sensor memory, and a sensor power supply,
the light detector, temperature sensor, signal amplifier, sensor processor, sensor memory, and sensor power supply in operable communication,
the scintillation material and light detector disposed within the sensor housing with the scintillation material adapted to receive a level of gamma radiation over the period of time from the in vivo radioactive analyte and to emit photons representative of the gamma radiation level, the light detector disposed with respect to the scintillation material so as to be adapted to receive and convert the multiplied photons into signal data representative of the frequency level over time of gamma radiation received,
the signal amplifier adapted to amplify the signal data, the sensor memory including a measurement sensor identifier, the measurement sensor having at least one sensor output port for such amplified signal data;
a measurement control device having a control processor, a non-transient control memory, a control power supply, and a clock,
the control processor, control memory, control power supply, and clock in operable communication,
the measurement control device having a control input port operably engaged with the sensor output port and adapted to receive amplified signal data from the measurement sensor;
wherein the control memory includes control computer program code executable by the control processor, the control computer program code including a first module for measurement, a second module for data management;
wherein the first module is adapted to receive the measurement sensor identifier, the signal data, and a subject identifier and to associate the signal data, sensor identifier, and measurement sensor identifier in a record file format;
a temperature compensator coupled with the temperature sensor, the temperature sensor adapted to measure an ambient temperature with the system adapted to communicate the ambient temperature to the temperature compensator, such that the temperature compensator is adapted to generate a temperature correction factor based on comparison of the ambient temperature to a reference temperature, the temperature compensator further adapted to apply the temperature correction factor to the signal data to produce temperature compensated signal data;
wherein the second module is adapted to receive the signal data of a record file from the first module and to transmit the compensated signal data to a desired storage; and
wherein the control computer program code further comprises a third module adapted to receive stored data of a record file from the second module, to apply such stored data to a predictive model to generate predictive data values over a desired period for such record file as a predictive outcome, and to transmit such predictive outcome to a desired storage.

2. The system of claim 1, wherein the sensor housing is substantially light proof.

3. The system of claim 2, wherein the housing defines an outer surface and comprises a light-proof coating on the outer surface.

4. The system of claim 1, wherein the sensor housing further comprises an adhesive adapted for removable attachment of the housing to the subject's skin.

5. The system of claim 1, wherein the system further comprises a measurement sensor carrier adapted to removably engage with the measurement sensor, the measurement sensor carrier defining a carrier surface, and a portion of the carrier surface comprises an adhesive adapted for removable attachment of the measurement sensor carrier to the subject's skin.

6. The system of claim 5, wherein the measurement sensor carrier defines at least one alignment feature for the removable alignment of the measurement sensor with respect to the subject.

7. The system of claim 1, wherein the sensor housing further comprises a shielding mask for gamma radiation.

8. The system of claim 7, wherein the shielding mask is selected from a group consisting of iridium, platinum, tungsten, gold, palladium, lead, silver, molybdenum, copper, nickel, bronze, brass, iron, steel, zinc, titanium, and aluminum.

9. The system of claim 1, wherein the measurement sensor further comprises:
   a light shield;
   a printed circuit board assembly having a board defining a plane having a first surface and an opposing second surface, the light shield adapted for mounting onto the first surface of the board and shielding the scintillation material and light detector from ambient light;
   wherein the scintillation material has first width parallel with the plane and the light detector has a second width parallel with the plane;
   the light shield defines a first cavity with a third width equal or greater than the first width such that the first cavity is adapted to receive the scintillation material and the light shield defines a second cavity with a fourth width equal or greater than the second width such that the second cavity is adapted to receive the light detector; and
   wherein the first and second cavities are in communication and in such proximal relation that the light shield optically aligns the scintillation material to the light detector when the scintillation material is received by the first cavity and the light detector is received by the second cavity, and operably engaged with the printed circuit board assembly.

10. The system of claim 9, further comprising a light emitter in operable communication with the sensor power supply, wherein the light shield is adapted to receive the light emitter proximal to the light detector.

11. The system of claim 1, wherein the measurement control device further comprises a display and data entry device.

12. The system of claim 1, wherein the control computer program code further comprises a third module adapted to receive stored data of a record file from the second module, to apply such stored data to calculate changes in the compensated signal data over a desired period, and to transmit such changes to a desired storage.

13. The system of claim 12,
   wherein the at least one ex vivo measurement sensor comprises a first and second measurement sensor, the first measurement sensor adapted to the ex vivo detection of test gamma radiation emitted by a subject from systemic administration of a radioactive analyte that decays in vivo by positron emission proximate to a test area, the second measurement sensor adapted to the ex vivo detection of background gamma radiation emitted by a subject from systemic administration of a radioactive analyte that decays in vivo by positron emission proximate to a background area;
   wherein the control computer program code further comprises a fourth module adapted to receive stored data of a record file from the second module including data from the first and second measurement sensors and to subtract signal data from the second measurement sensor from signal data from the first measurement sensor.

14. The system of claim 1, wherein the control computer program code further comprises a third module adapted to receive stored data of a record file from the second module, to apply such stored data to calculate changes in the compensated signal data from background radiation data over a desired period, and to transmit such changes to a desired storage.

15. The system of claim 1, wherein the scintillation material is selected from a group consisting of bismuth germanate, gadolinium oxyorthosilicate, cerium-doped lutetium oxyorthosilicate, cerium-doped yttrium oxyorthosilicate, sodium iodide, thallium-doped sodium iodide, polyvinyltoluene, and cadmium zinc telluride.

16. The system of claim 1, wherein the sensor power supply is a microelectromechanical machine adapted to generate electricity.

17. The system of claim 1, wherein the control input port is operably engaged with the sensor output port by cable.

18. The system of claim 1, wherein the control input port is operably engaged with the sensor output port by wireless communication.

19. The system of claim 1, wherein the signal data comprises a plurality of pulses at a pulse frequency over time, and wherein the first module is adapted to communicate a sampling frequency instruction to the sensor processor, the sampling frequency instruction being a function of the pulse frequency of the signal data.

20. The system of claim 19, wherein the first module is adapted to communicate an increasing sampling frequency instruction upon an increase in pulse frequency.

21. A system for the ex vivo real-time detection of gamma radiation emitted by a subject from systemic administration and uptake of a radioactive analyte that decays in vivo over a period of time by positron emission, the system comprising:
   at least one ex vivo measurement sensor having a sensor housing, a scintillation material, a light detector, a temperature sensor, a signal amplifier, a sensor processor, a non-transient sensor memory, and a sensor power supply,
      the light detector, temperature sensor, signal amplifier, sensor processor, sensor memory, and sensor power supply in operable communication,
      the scintillation material and light detector disposed within the sensor housing with the scintillation material adapted to receive a level of gamma radiation over the period of time from the in vivo radioactive analyte and to emit photons representative of the gamma radiation level, the light detector disposed with respect to the scintillation material so as to be adapted to receive and convert the multiplied photons into signal data representative of the frequency level over time of gamma radiation received,
      the signal amplifier adapted to amplify the signal data, the sensor memory including a measurement sensor identifier, the measurement sensor having at least one sensor output port for such amplified signal data;
   a measurement control device having a control processor, a non-transient control memory, a control power supply, and a clock,
      the control processor, control memory, control power supply, and clock in operable communication,
      the measurement control device having a control input port operably engaged with the sensor output port and adapted to receive amplified signal data from the measurement sensor;
   wherein the control memory includes control computer program code executable by the control processor, the control computer program code including a first module for measurement, a second module for data management;
   wherein the first module is adapted to receive the measurement sensor identifier, the signal data, and a subject identifier and to associate the signal data, sensor identifier, and measurement sensor identifier in a record file format;
   a temperature compensator coupled with the temperature sensor, the temperature sensor adapted to measure an ambient temperature with the system adapted to communicate the ambient temperature to the temperature compensator, such that the temperature compensator is adapted to generate a temperature correction factor based on comparison of the ambient temperature to a reference temperature, the temperature compensator further adapted to apply the temperature correction factor to the signal data to produce temperature compensated signal data;

wherein the second module is adapted to receive the signal data of a record file from the first module and to transmit the compensated signal data to a desired storage;

a processing station in communication with the measurement control device, the station having a station processor, a non-transient station memory, a station power supply, the station processor, station memory, station power supply in operable communication, the processing station having a station input port operably engaged with the control output port and adapted to receive data from the measurement control device;

wherein the station memory includes station computer program code executable by the station processor, the station computer program code including a third module adapted to receive stored data of a record file from the second module, to apply such stored data to a predictive model to generate predictive data values over a desired period for such record file as a predictive outcome.

22. The system of claim 21, wherein the predictive model is a classification machine learning model.

23. The system of claim 21, wherein the predictive model is an unsupervised cluster analysis.

24. The system of claim 23, wherein the predictive model is an unsupervised cluster analysis adapted to predicting future outcome, predicting an effect of tumor treatment, and predicting metastasis.

25. The system of claim 21, wherein the processing station further comprises a docking device in operable communication with the station processor, the docking device adapted to receive the measurement control device, the docking device having an electrical connector that engages with measurement control device for data communication and power exchange.

26. The system of claim 21,
wherein the at least one ex vivo measurement sensor comprises a first and second measurement sensor, the first measurement sensor adapted to the ex vivo detection of test gamma radiation emitted by a subject from systemic administration of a radioactive analyte that decays in vivo by positron emission proximate to a test area, the second measurement sensor adapted to the ex vivo detection of background gamma radiation emitted by a subject from systemic administration of a radioactive analyte that decays in vivo by positron emission proximate to a background area;
wherein the station computer program code includes a fourth module adapted to receive stored data of a record file from the second module including data from the first and second measurement sensors, and to subtract signal data from the second measurement sensor from signal data from the first measurement sensor.

27. A system for the real-time detection of gamma radiation emitted by a subject from systemic administration and uptake of a radioactive analyte that decays by positron emission over a period of time, the system comprising:
at least one in vivo measurement sensor having a hermetically sealed sensor housing of biocompatible material, a scintillation material, a light detector, a signal amplifier, a sensor processor, a non-transient sensor memory, and a sensor power supply,
the light detector, signal amplifier, sensor processor, sensor memory, and sensor power supply in operable communication,
the light detector having an active area and the scintillation material is configured to substantially match the active area, the scintillation material and light detector disposed within the sensor housing with the scintillation material adapted to receive a level of gamma radiation over the period of time from the in vivo radioactive analyte and to emit photons representative of the gamma radiation level, the light detector disposed with respect to the scintillation material so as to be adapted to receive and convert the multiplied photons into signal data representative of the frequency level over time of gamma radiation received,
the signal amplifier adapted to amplify the signal data,
the sensor memory including a measurement sensor identifier, the measurement sensor having at least one wireless sensor output port for such amplified signal data;
an ex vivo measurement control device having a control processor, a non-transient control memory, a control power supply, and a clock,
the control processor, control memory, control power supply, and clock in operable communication,
the measurement control device having a wireless control input port operably engaged with the wireless sensor output port and adapted to receive amplified signal data from the measurement sensor;
wherein the control memory includes control computer program code executable by the control processor, the control computer program code including a first module for measurement, a second module for data management;
wherein the first module is adapted to receive the measurement sensor identifier, the amplified signal data, and a subject identifier and to associate the signal data, sensor identifier, and measurement sensor identifier in a record file format;
wherein the second module is adapted to receive the amplified signal data of a record file from the first module and to transmit the amplified signal data to a desired storage; and
a third module, wherein the third module is adapted to receive stored data of a record file from the second module, to apply such stored data to a predictive model to generate predictive data values over a desired period for such record file as a predictive outcome, and to transmit such predictive outcome to a desired storage.

28. The system of claim 27, wherein the biocompatible material is selected from a group consisting of glass, polyether ether ketone, and ultra-high-molecular-weight polyethylene.

29. The system of claim 27, wherein the sensor housing defines an outer surface and the sensor housing further comprises an anchor disposed on the sensor housing outer surface.

30. The system of claim 29, wherein
the sensor housing is substantially tubular and defines a sensor housing length;
the wireless sensor output port comprises an antenna running substantially along the length of the sensor housing; and
the anchor comprises at least one raised ring about a portion of a circumference of the sensor housing, the at least one raised ring disposed on the outer surface and having a height from the outer surface of about 0.1 mm to 3 mm.

31. The system of claim 27, wherein the third module is further adapted to apply such stored data to calculate changes in the amplified signal data over a desired period, and to transmit such changes to a desired storage.

32. The system of claim 27, wherein the third module adapted to apply such stored data to calculate changes in the amplified signal data from background radiation data over a desired period, and to transmit such changes to a desired storage.

33. The system of claim 27, wherein the signal data comprises a plurality of pulses at a pulse frequency over time, and wherein the first module is adapted to communicate a sampling frequency instruction to the sensor processor, the sampling frequency instruction being a function of the pulse frequency of the signal data.

34. The system of claim 33, wherein the first module is adapted to communicate an increasing sampling frequency instruction upon an increase in pulse frequency.

* * * * *